US006685948B1

United States Patent
Zeng et al.

(10) Patent No.: US 6,685,948 B1
(45) Date of Patent: Feb. 3, 2004

(54) REPLICATION-DEFECTIVE DENGUE VIRUSES THAT ARE REPLICATION-DEFECTIVE IN MOSQUITOES FOR USE AS VACCINES

(75) Inventors: Lingling Zeng, Brooklyn, NY (US); Lewis Markoff, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/798,542

(22) Filed: Mar. 2, 2001

Related U.S. Application Data

(63) Continuation of application No. PCT/US99/02598, filed on Feb. 5, 1999.
(60) Provisional application No. 60/098,981, filed on Sep. 2, 1998.

(51) Int. Cl.[7] .......................... A61K 39/12; C12P 19/30; C12N 7/00; C12N 7/01; C12N 7/04
(52) U.S. Cl. ........................... 424/218.1; 424/204.1; 435/91.33; 435/235.1; 435/236
(58) Field of Search .............................. 435/235.1, 236, 435/239, 91.33; 536/23.1, 24.1, 24.2; 424/218.1, 204.1

(56) References Cited

FOREIGN PATENT DOCUMENTS

WO    WO 93/06214    *    4/1993

OTHER PUBLICATIONS

Chambers et al. Annual Review of Microbiology. 1990; 44: 649–88.*
Zeng et al. Journal of Virology. Sep. 1998; 72 (9): 7510–7522.*
Markoff et al. Journal of Virology. 2002; 76 (7): 3318–3328.*
Grange, T., et al. (1985) Stable secondary structures at 3'–end of the genome of yellow fever virus (17 D vaccine strain). FEBS Lett. 188(1):159–163.
Irie, K., et al. (1989) Sequence analysis of cloned dengue virus type 2 genome (New Guinea C strain). Gene 75:197–211.
Jacobson, S. J., et al. (1993) Biochemical and genetic evidence for a pseudoknot structure at the 3' terminus of the poliovirus RNA genome and its role in viral RNA amplification. J. Virol. 67(6):2961–2971.
Kuhn, R. J et al. (1992) Attenuation of Sindbis virus neurovirulence by using defined mutations in nontranslated regions of the genome RNA. J. Virol. 66(12):7121–7127.
Li, W., et al. (1996) Effect of West Nile virus (WNV) 5' and 3' regions on translation. Abstracts of the American Society for Virology 15th Annual Meeting., Abstr. W2–1, p. 85.

Men, R., et al. (1996) Dengue type 4 virus mutants containing deletions in the 3' noncoding region of the RNA genome: analysis of growth restriction in cell culture and altered viremia pattern and immunogenicity in rhesus monkeys. J. Virol. 70(6):3930–3937.
Mohan, P. M., et al. (1991) Detection of stable secondary structure at the 3' terminus of dengue virus type 2 RNA. Gene 108:185–191.
Monath, T. P. (1994) Dengue: the risk to developed and developing countries. Proc. Natl. Acad. Sci. USA 91:2395–2400.
Pogue, G. P., et al. (1996) Autoantigens interact with cis–acting elements of rubella virus RNA. J. Virol. 70(9):6269–6277.
Polo, S., et al. (1997) Infectious RNA transcripts from full–length dengue virus type 2 cDNA clones made in yeast. J. Virol. 71(7):5366–5374.
Rice, C. M., et al. (1985) Nucleotide sequence of yellow fever virus: implications for flavivirus gene expression and evolution. Science 229:726–733.
Schägger, H., et al. (1987) Tricine–sodium dodecyl sulfate–polyacrylamide gel electrophoresis for the separation of proteins in range from 1 to 100 kDa. Anal. Biochem. 166:368–379.
Sherman, F. (1991) Getting started with yeast. Methods Enzymol. 194:3–21.
Shi, P.–Y., et al. (1996) Evidence for the existence of a pseudoknot structure at the 3' terminus of the flavivirus genomic RNA. Biochemistry 35:4222–4230.

(List continued on next page.)

*Primary Examiner*—James Housel
*Assistant Examiner*—Shanon Foley
(74) *Attorney, Agent, or Firm*—Knobbe, Martens, Olson & Bear LLP

(57) ABSTRACT

The present invention is directed toward vector stage replication-defective flaviviruses that are replication-defective in mosquito vectors that transmit them to humans. Such mutant flaviviruses may be useful as vaccines. The replication-defective flaviviruses of the present invention demonstrate a limited ability to replicate in the vector organisms that transmit flaviviruses from one host to another. More specifically, the present invention is directed toward the construction and propagation of flaviviruses that possess 3'-noncoding regions altered in such a way as to prevent or severely limit viral reproduction in a vector organism. In one embodiment of the present invention, a replication-defective dengue virus that is replication-defective in arthropods is contemplated for use as a vaccine. In another embodiment, a replication-defective dengue virus that is replication-defective in mosquitoes is contemplated for use as a vaccine. The present invention also contemplates methods of producing such mutant flaviviruses for use as vaccines as well as methods that induce a protective immunity against flavivirus infection or disease in an immunized subject.

18 Claims, 11 Drawing Sheets

OTHER PUBLICATIONS

Shi, P.-Y., et al. (1996) Cell proteins bind specifically to West Nile virus minus–strand 3' stem–loop RNA. J. Virol. 70(9):6278–6287.

Spencer, F., et al. (1993) Targeted recombination–based cloning and manipulation of large DNA segments in yeast. Methods: Companion to Methods Enzymol. 5:161–175.

Stern, S., et al. (1986) Location of the binding site for protein S4 on 16 S Ribosomal RNA by chemical and enzymatic probing and primer extension. J. Mol. Biol. 192:101–110.

Stollar, V., et al. (1967) Studies of the nature of dengue viruses. III. RNA synthesis in cells infected with type 2 dengue virus. Virology 33:650–658.

Takegami, T., et al. (1986) Nucleotide sequence at the 3' end of Japanese encephalitis virus genomic RNA. Virology 152:483–486.

Tan, B.-H., et al. (1996) Recombinant denque type 1 virus NS5 protein expressed in *Escherichia coli* RNA–dependent RNA polymerase activity. Virology 216:317–325.

Valle, R. P. C., et al. (1993) Elimination of L–A double–stranded RNA virus of *Saccharomyces cerevisiae* by expression of gag and gap–pol from an L–A cDNA clone. J. Virol. 67(5):2764–2771.

Weeks, K. M., et al. (1991) RNA recognition by Tat–derived peptides: interaction with the major groove? Cell 66:577–588.

Wengler, G., et al. (1986) Analysis of structural properties which possibly are characteristic for the 3'–terminal sequence of the genome RNA of flaviviruses. J. Gen. Virol. 67:1183–1188.

Wu, H.-N., et al. (1987) Role of a bulged A residue in a specific RNA–protein interaction. Biochemistry 26:8221–8227.

Zeng, L., et al. (1998) Identification of specific nucleotide sequences within the conserved 3'–SL in the Dengue type 2 virus genome required for replication. J. Virol. 72(9):7510–7522.

PCT Notification of Transmittal of the International Search Report for Intl. Appl. No. PCT/US99/02598.

Atreya, C. D., et al., (1995) The rubella virus RNA binding activity of human calreticulin is localized to the N–terminal domain. J. Virol. 69(6):3848–3851.

Bartel, D. P., et al. (1991) HIV–1 Rev regulation involves recognition of non–Watson–Crick base pairs in the viral RNA. Cell 67:529–536.

Blackwell, J. L., et al. (1995) BHK cell proteins that bind to the 3' stem–loop structure of the West Nile virus genome RNA. J. Virol. 69(9):5650–5658.

Blackwell, J. L., et al. (1997) Translation elongation factor–1 alpha interacts with the 3' stem–loop region of West Nile virus genomic RNA. J. Virol. 71(9):6433–6444.

Brinton, M. A. (1986) Replication of flaviviruses, S. Schlesinger, and M. Schlesinger (ed.), The Togaviridae and the Flaviviridae. p. 327–374. Plenum Press, New York, N.Y.

Brinton, M. A., et al. (1986) The 3'–nucleotides of flavivirus genomic RNA form a conserved secondary structure. Virology 153:113–121.

Brinton, M. A., et al. (1988) Sequence and secondry structure analysis of the 5'–terminal region of flavivirus genome RNA. Virology 162:290–299.

Cahour, A., et al. (1995) Growth–restricted dengue virus mutants containing deletions in the 5' noncoding region of the RNA genome. Virology 207:68–76.

Chambers, T. J., et al. (1990) Flavivirus genome organization, expression, and replication. Annu. Rev. Microbiol. 44:649–688.

Chen, C.-J., et al. (1997) RNA–protein interactions: involvement of NS3, NS5, and 3' noncoding regions of Japanese encephalitis virus genomic RNA. J. Virol. 71(5):3466–3473.

* cited by examiner

Fig.2

(top)
(bottom)

D2-SL

WN-SL

D2/WN-SL(mutA)

D2/WN-SL(mutB)

D2/WN-SL(mutC)

D2/WN-SL(mutD)

D2/WN-SL(mutE)

D2/WN-SL(mutF)

| VIRUS | DAYS POST-ELECTROPORATION | | | |
|---|---|---|---|---|
| | 5 | 10 | 15 | 20 |
| DEN2 wt | ■ | ■ | | |
| D2/WN-SL | ■ | ■ | ■ | ■ |
| (mutA) | ■ | ■ | ■ | |
| (mutD) | ■ | ■ | ■ | ■ |
| (mutE) | ■ | ■ | ■ | ■ |
| (mutF) | ■ | ■ | ■ | ■ |

Replication of mutF virus in monkey kidney cells is associated with a spontaneous deletion mutation within the 3'-SL (A) MutF in input RNA

```
----G
75 U—C
   C—G
   U—A
   A—U  A3
      |   ↑ dIA3
   G—C
80 A—U1 (3'-terminus)
```

(B) MutF in replicating virus RNA

```
----G
   U—C
   C—G
76 U A—U4
   A—U
   G—C
79 A—U3'
```

(C) wt DEN2 analogous nt sequence

```
----A
   U—G
   C—G
76 U A—U4
   A—U
   G—C
79 A—U3'
```

(D) wt WN nt sequence per Castle & Wengler

```
----A
   U—G
   C—G
   U—A
   A—U
   G—C
79 G—U3'
```

|  | LLC-MK2 | C6/36 |
|---|---|---|
| uninfected cell control | | |
| WT DEN2 | ● | ● |
| D2/WN-SL(mutA) | ▬ | ▬ |
| D2/WN-SL(mutD) | ▬ | — |
| D2/WN-SL(mutF) | | |
| D2-SL(A) | — | — |
| D2-SL(b) | — | — |

SEQUENCE LISTING

```
<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
gcatggcgta gtggactagc gg                                              22

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
atgattacgc caagcgcgc                                                  19

<210> SEQ ID NO 3
<211> LENGTH: 93
<212> TYPE: RNA
<213> ORGANISM: Flavivirus, Dengue Type 2

<400> SEQUENCE: 3
ucuuggacaa cuaaguuguc gugguaaggu aaaagaccgc aagacacgga ccuuacuacg     60
acuccucugu cguccuagag accagaaagg guc                                  93

<210> SEQ ID NO 4
<211> LENGTH: 96
<212> TYPE: RNA
<213> ORGANISM: Flavivirus, West Nile

<400> SEQUENCE: 4
ucauaggaca caagagcgug guggucggug guaacagccg cgugacacgg cacaccgacc     60
aacacgucuc gucuucuaga ggaccagaua gggucc                               96

<210> SEQ ID NO 5
<211> LENGTH: 45
<212> TYPE: RNA
<213> ORGANISM: Flavivirus, Dengue Type 2

<400> SEQUENCE: 5
```

```
gucgugguaa gguaaaagac cgcaagacac ggaccuuacu acgac           45

<210> SEQ ID NO 6
<211> LENGTH: 50
<212> TYPE: RNA
<213> ORGANISM: Flavivirus, West Nile

<400> SEQUENCE: 6
cguggugguc gguguaaca gccgcgugac acggcacacc gaccaacacg       50

<210> SEQ ID NO 7
<211> LENGTH: 17
<212> TYPE: RNA
<213> ORGANISM: Flavivirus, Dengue Type 2

<400> SEQUENCE: 7
ucuuggacaa cuaaguu                                          17

<210> SEQ ID NO 8
<211> LENGTH: 31
<212> TYPE: RNA
<213> ORGANISM: Flavivirus, Dengue Type 2

<400> SEQUENCE: 8
uccucugucg uccaguguac cagaaagggu c                          31

<210> SEQ ID NO 9
<211> LENGTH: 16
<212> TYPE: RNA
<213> ORGANISM: Flavivirus, West Nile

<400> SEQUENCE: 9
ucauaggaca caagag                                           16

<210> SEQ ID NO 10
<211> LENGTH: 30
<212> TYPE: RNA
<213> ORGANISM: Flavivirus, West Nile

<400> SEQUENCE: 10
ucucgucuuc uagaggacca gauagggucc                            30

<210> SEQ ID NO 11
<211> LENGTH: 17
<212> TYPE: RNA
<213> ORGANISM: Flavivirus, West Nile

<400> SEQUENCE: 11
uccucugucg uccuaga                                          17

<210> SEQ ID NO 12
<211> LENGTH: 14
<212> TYPE: RNA
<213> ORGANISM: Flavivirus, West Nile

<400> SEQUENCE: 12
ucucgucuuc uaga                                             14

<210> SEQ ID NO 13
<211> LENGTH: 14
<212> TYPE: RNA
<213> ORGANISM: Flavivirus, Dengue Type 2

<400> SEQUENCE: 13
```

```
gaccagaaag gguc                                                    14

<210> SEQ ID NO 14
<211> LENGTH: 16
<212> TYPE: RNA
<213> ORGANISM: Flavivirus, West Nile

<400> SEQUENCE: 14
ggaccagaua gggucc                                                  16

<210> SEQ ID NO 15
<211> LENGTH: 11
<212> TYPE: RNA
<213> ORGANISM: Flavivirus, Dengue Type 2

<400> SEQUENCE: 15
acaacuaagu u                                                       11

<210> SEQ ID NO 16
<211> LENGTH: 11
<212> TYPE: RNA
<213> ORGANISM: Flavivirus, Dengue Type 2

<400> SEQUENCE: 16
uccucugucg u                                                       11

<210> SEQ ID NO 17
<211> LENGTH: 10
<212> TYPE: RNA
<213> ORGANISM: Flavivirus, West Nile

<400> SEQUENCE: 17
gacacaagag                                                         10

<210> SEQ ID NO 18
<211> LENGTH: 9
<212> TYPE: RNA
<213> ORGANISM: Flavivirus, West Nile

<400> SEQUENCE: 18 ucucgucuu                                                          9

<210> SEQ ID NO 19
<211> LENGTH: 7
<212> TYPE: RNA
<213> ORGANISM: Flavivirus, Dengue Type 2

<400> SEQUENCE: 19 uguugga                                                            7

<210> SEQ ID NO 20
<211> LENGTH: 7
<212> TYPE: RNA
<213> ORGANISM: Flavivirus, Dengue Type 2

<400> SEQUENCE: 20 uccuaga                                                            7

<210> SEQ ID NO 21
<211> LENGTH: 7
<212> TYPE: RNA
<213> ORGANISM: Flavivirus, West Nile
```

```
<400> SEQUENCE: 21 ucauagg                                                           7

<210> SEQ ID NO 22
<211> LENGTH: 6
<212> TYPE: RNA
<213> ORGANISM: Flavivirus, West Nile

<400> SEQUENCE: 22 ucuaga                                                            6

<210> SEQ ID NO 23
<211> LENGTH: 6
<212> TYPE: RNA
<213> ORGANISM: Flavivirus, Dengue Type 2

<400> SEQUENCE: 23 guaagg                                                            6

<210> SEQ ID NO 24
<211> LENGTH: 6
<212> TYPE: RNA
<213> ORGANISM: Flavivirus, Dengue Type 2

<400> SEQUENCE: 24 ccuuac                                                            6

<210> SEQ ID NO 25
<211> LENGTH: 12
<212> TYPE: RNA
<213> ORGANISM: Flavivirus, Dengue Type 2

<400> SEQUENCE: 25
gucgugguaa gg                                                    12

<210> SEQ ID NO 26
<211> LENGTH: 12
<212> TYPE: RNA
<213> ORGANISM: Flavivirus, Dengue Type 2

<400> SEQUENCE: 26
ccuuacuacg ac                                                    12

<210> SEQ ID NO 27
<211> LENGTH: 7
<212> TYPE: RNA
<213> ORGANISM: Flavivirus, West Nile

<400> SEQUENCE: 27 ucauagg                                                           7

<210> SEQ ID NO 28
<211> LENGTH: 7
<212> TYPE: RNA
<213> ORGANISM: Flavivirus, West Nile

<400> SEQUENCE: 28 ucuaggc                                                           7
```

REPLICATION-DEFECTIVE DENGUE VIRUSES THAT ARE REPLICATION-DEFECTIVE IN MOSQUITOES FOR USE AS VACCINES

This application is a continuation of prior application International Application No. PCT/US99/02598 having international filing date of Feb. 5, 1999, designating the United States of America and published in English, which claims priority of U.S. Application No. 60/098,981 filed Sep. 2, 1998.

BACKGROUND OF THE INVENTION

Dengue (DEN) viruses belong to the genus flavivirus, within the family Flaviviridae. There are at least 70 flavivirus species, among which the most important human pathogens are the DEN viruses, yellow fever virus, and the Japanese (JE) and tick-borne encephalitis viruses. Diseases caused by the 4 serotypes of DEN virus (DEN1–4), dengue fever (DF) or dengue hemorrhagic fever/shock syndrome (DHF/DSS), are endemic or epidemic in tropical and subtropical countries around the world.

In a manner similar to that of yellow fever, dengue is transmitted between humans by the domestic mosquito vector, *Aedes aegypti*. Evidence has emerged for the existence of a sylvan cycle of transmission analogous to that of yellow fever, involving monkeys and several sylvatic Aedes species. Transovarial transmission has been demonstrated experimentally in these forest mosquito species.

In light of this evidence, a model of dengue fever transmission where the virus emerges from the jungle to infect urban populations may be suggested. In this model, monkeys serve as a reservoir for the virus and transmission of the virus from monkey to monkey occurs through a mosquito vector. According to this model, the virus is transmitted from mosquito to human and then from that infected human to other mosquitoes of the species *Aedes aegypti*. Once these mosquitoes are infected, the dengue virus is transmitted to other human hosts. These infected individuals then pass the dengue virus on to other *Aedes aegypti* mosquitoes and expand the range of infection. Person-to-person spread of dengue virus infection and disease does not occur.

At present, because of several demanding technical problems, there is no vaccine available to prevent the diseases caused by dengue virus infection (DF and DHF/DSS). For example, a suitable live virus vaccine ought not to replicate efficiently in the mosquito vector, since it is conceivable that a live, attenuated vaccine could revert to full virulence during replication in a mosquito that has fed on a vaccinee. Thus, a local or regional immunization program could lead to the spread of illness rather than the diminution of disease incidence in the vaccinated population. Accordingly, a safe and effective dengue virus vaccine will have a severely limited ability to be transmitted from human host to mosquito vector. The present invention seeks to provide such a vaccine and solve the long felt need for safe and effective vaccines directed to the known serotypes of dengue as well as to provide vaccines for other flaviviruses.

SUMMARY OF THE INVENTION

The flavivirus genome is a positive-stranded ~11-kb RNA including 5'- and 3'-noncoding regions (NCR) of approximately 100 and 400 to 600 nucleotides, respectively. The 3'-NCR contains adjacent, thermodynamically stable, conserved short and long stem and loop structures (the 3'-SL), formed by the 3'-terminal ~100 nucleotides. The nucleotide sequences within the 3'-SL are not well conserved among species. The requirement for the 3'-SL for replication was examined in the context of dengue virus, type 2, (DEN2) replication, by mutagenesis of an infectious cDNA copy of a DEN2 genome. Genomic full-length RNA was transcribed in vitro and used to transfect monkey kidney cells. A substitution mutation, in which the 3'-terminal 93 nucleotides comprising the wild type DEN2 3'-SL sequence were replaced by the 96 nucleotide sequence of the West Nile virus (WN) 3'-SL, was sublethal for virus replication. Analysis of the growth phenotypes of additional mutant viruses derived from RNAs containing DEN2-WN chimeric 3'-SL structures suggested that the wild type DEN2 nucleotide sequence forming the bottom half of the long stem and loop in the 3'-SL was required for viability. One 7 base pair substitution mutation in this domain resulted in a mutant virus that grew well in monkey kidney cells but was severely restricted in cultured mosquito cells. In contrast, transpositions and/or substitutions of the wild type DEN2 nucleotide sequence in the top half of the long stem and in the short stem and loop were relatively well tolerated, provided the stem-loop secondary structure was conserved. A mutant dengue virus that was observed to be replication-defective in mosquito cells in tissue culture was also shown to be replication-defective in adult mosquitoes. The methods discussed herein also contemplate utility for use against any flavivirus, since the 3'-SL structure is conserved among all the more than 20 flavivirus genomes that have been subjected to nucleotide sequence analysis to date.

BRIEF DESCRIPTION OF THE DRAWINGS

FIG. 2 shows a graphical representation of the conformation and 96 nucleotide sequence of the WN 3'-SL. Nucleotides are numbered beginning from the 3'-terminus of the genome. The "top" and "bottom" portions were previously defined in FIG. 1. Segments of the WN 3'-SL nucleotide sequence that were substituted for the corresponding DEN2 nucleotide sequences in DEN2-WN chimeric RNAs are indicated by brackets labeled with the names of the resultant chimeric viruses.

FIG. 4 shows photographs taken of an indirect immunofluorescence assay (IFA) for growth of DEN2 wild type and DEN2-WN chimeric mutant viruses.

FIG. 8 shows growth curves for wild type and viable mutant DEN2 viruses where virus stocks were used to infect C6/36 cells.

FIG. 9 shows a graphical representation of 3'-SL structures and the locus of a spontaneous mutation in the 3'-SL of D2/WN-SL(mutF) RNA associated with replication in monkey kidney cells and its effect on 3'-SL structure. Nucleotides are numbered from the 3'-terminus of the RNA genome.

FIG. 10 shows an autoradiogram of a Northern blot hybridization of viral RNAs in infected LLC-MK2 and C6/36 cells.

FIG. 11 shows an autoradiogram of a Western blot hybridization of viral proteins in infected LLC-MK2 cells.

DETAILED DESCRIPTION OF THE INVENTION

Figure 1:
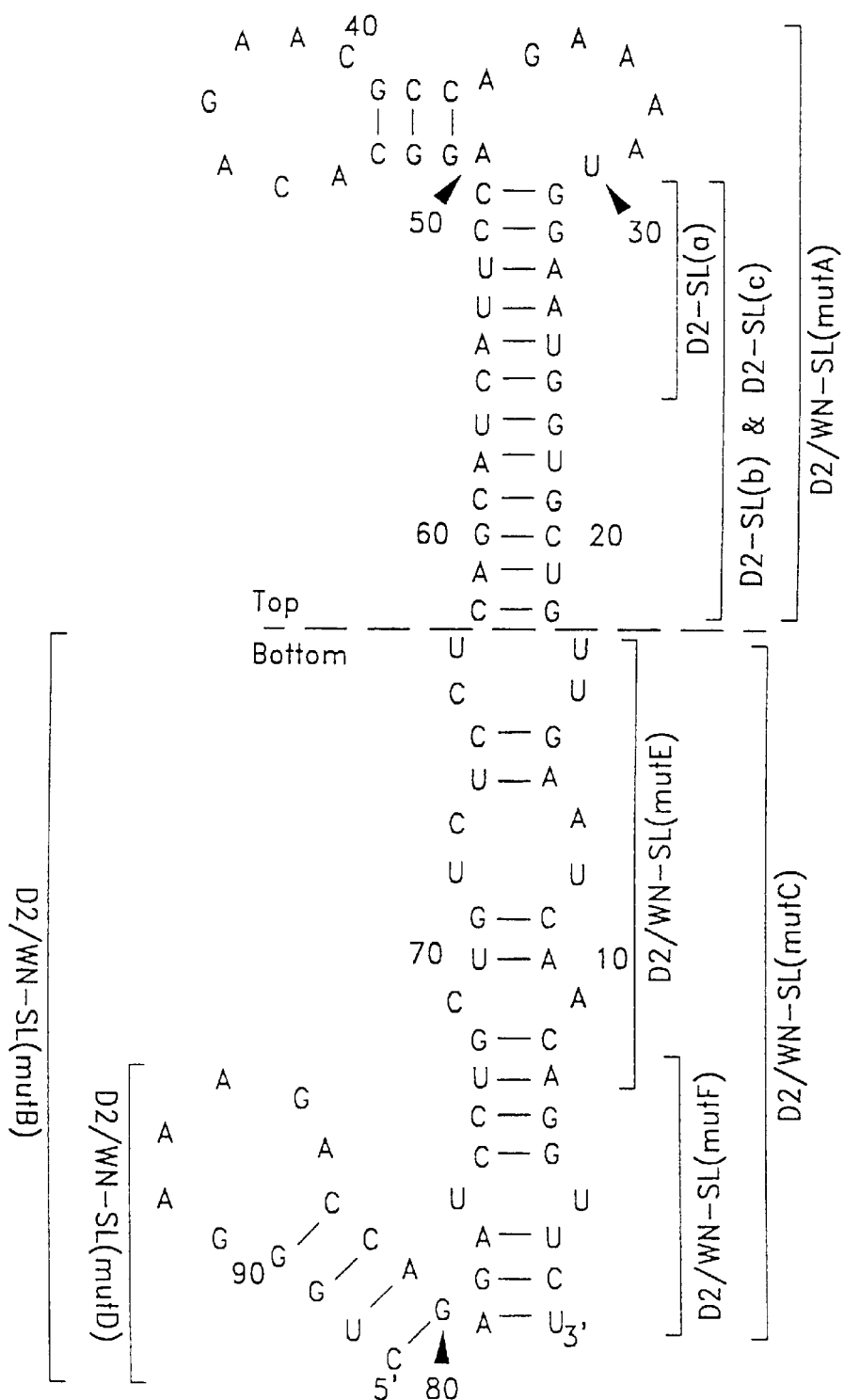
FIG. 1 shows a graphical representation of the proposed conformation and 93 nucleotide sequence of the dengue, type 2 (DEN2) 3'-SL. Nucleotides are numbered from the 3'-terminus of the DEN2 genome. For the purposes of this study, the DEN2 3'-SL was divided into "top" and "bottom" portions according to an approach taken for the 3'-SL of West Nile virus (WN) strain E101. Segments of the DEN2 3'-SL that were mutagenized are indicated by brackets, labeled with the names of the respective mutant viruses.

The present invention is directed toward vector stage replication-defective flaviviruses that are replication-defective in mosquito vectors that transmit them to humans. Such mutant flaviviruses may be useful as vaccines. The replication-defective flaviviruses of the present invention demonstrate a limited ability to replicate in the vector organisms that transmit flaviviruses from one host to another. More specifically, the present invention is directed toward the construction and propagation of flaviviruses that possess 3'-noncoding regions altered in such a way as to prevent or severely limit viral reproduction in a vector organism. In one embodiment of the present invention, a replication-defective dengue virus that is replication-defective in arthropods is contemplated for use as a vaccine. In another embodiment, a replication-defective dengue virus that is replication-defective in mosquitoes is contemplated for use as a vaccine. The present invention also contemplates methods of producing such mutant flaviviruses for use as vaccines as well as methods that induce a protective immunity against flavivirus infection or disease in an immunized subject.

The family Flaviviridae comprises at least 70 viruses, 67 of which are arthropod-borne. Of the 67 arboviruses, 34 are mosquito-borne and 19 are tick-borne. Examples of viruses contemplated for use with the present invention include: Banzi, Bussuquara, Dengue (types 1–4), Edge Hill, Hanazalova, Hypr, Ilheus, Israel turkey meningoencephalitis, Japanese encephalitis, tick-borne encephalitis, Kedougou, Kokobera, Koutango, Kumlinge, Kunjin, Kyasanur Forest disease, Langat, Louping ill, Modoc, Murray valley encephalitis, Negishi, Omsk hemorrhagic fever, Powassan, Rocio, Russian spring-summer encephalitis, St. Louis encephalitis, Sepik, Spondweni, Usutu, Wesselsbron, West Nile, Yellow fever, and Zika. More than half of the 67 arboviruses are associated with human disease, including the most important arthropod-borne viral afflictions of humankind-dengue fever, yellow fever, tick-borne encephalitis, and Japanese encephalitis. A number of flaviviruses, e.g., Israel turkey meningoencephalitis, Japanese encephalitis, Kyasanur Forest disease, Louping ill, West Nile and Murray valley encephalitis are pathogenic for domestic or wild animals of economic importance.

Although flaviviruses are the cause a great deal of human suffering and economic loss, there is a shortage of effective vaccines. Replication-defective vaccines are most often live, attenuated infectious viruses, killed viruses, or purified subunits of killed viruses. Ideally, live, attenuated viral vaccines possess a limited ability to replicate in the immunized subject yet induce a strong immune response. Utilization of this strategy against flavivirus infection is complicated. Replication of a vaccine virus in the vector may lead to the spread of a virulent revertant virus in the non-immune population.

It is conceivable that an immunization program using an attenuated flavivirus vaccine, for example, a dengue virus vaccine, could spread that virus to mosquitoes that would, in turn, spread it to other human beings. This scenario might prove dangerous if the attenuated virus were to regain its virulence during its replication in the mosquito arthropod vector. Accordingly, flaviviruses that are replication-defective in the vector stage of the viral life cycle, in which the virus resides in the arthropod vector host yet demonstrates a reduced capability to reproduce, would be especially advantageous. Such flaviviruses are contemplated by the present invention for use as vaccines.

The flavivirus genome is a single-stranded, positive-sense ~11-kb RNA. It contains a single long open reading frame which includes 95% of the nucleotide sequence. The encoded polyprotein is processed to produce three structural proteins (capsid, premembrane, and envelope) and seven non-structural proteins (NS1, NS2A, NS2B, NS3, NS4A, NS4B, and NS5. The 5'- and 3'-noncoding regions (NCR) of flavivirus genomes are approximately 100 and 400–600 nucleotides in length, respectively. These segments are expected to include promoter elements for full-length positive and negative sense RNA synthesis, since current evidence suggests that no subgenomic-size RNAs are synthesized during virus replication.

Figure 3:
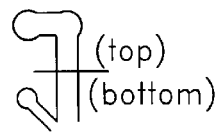
FIG. 3 shows a graphical representation of the composition of the 3'-SL contained in the mutant viruses.
Figure 3:
Figure 3:
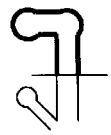
Figure 3:
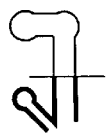
Figure 3:
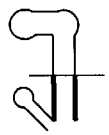
Figure 3:
Figure 3:
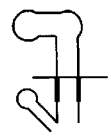
Figure 3:
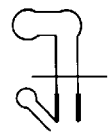

The terminal nucleotide sequences of both NCRs in flavivirus RNA are predicted to form stem-and-loop secondary structures. The 3'-terminal secondary structure includes a "short" stem and loop adjacent to a "long" stem and loop (the "3'-SL"). For the purposes of the present invention, the stem-loop structures of the 3'-NCR are divided into descriptive regions for mapping the various mutations. Here, the 3' stem-loop structure is divided into "top" and "bottom" halves as illustrated in FIG. 3. It can also be divided into the small stem and loop and the long stem and loop. Additionally, the long stem and loop can be divided into the "top" and "bottom" halves, and the bottom half of the long stem and loop structure can be further sub-divided into an upper-most portion and a lower most portion.

Figure 2:
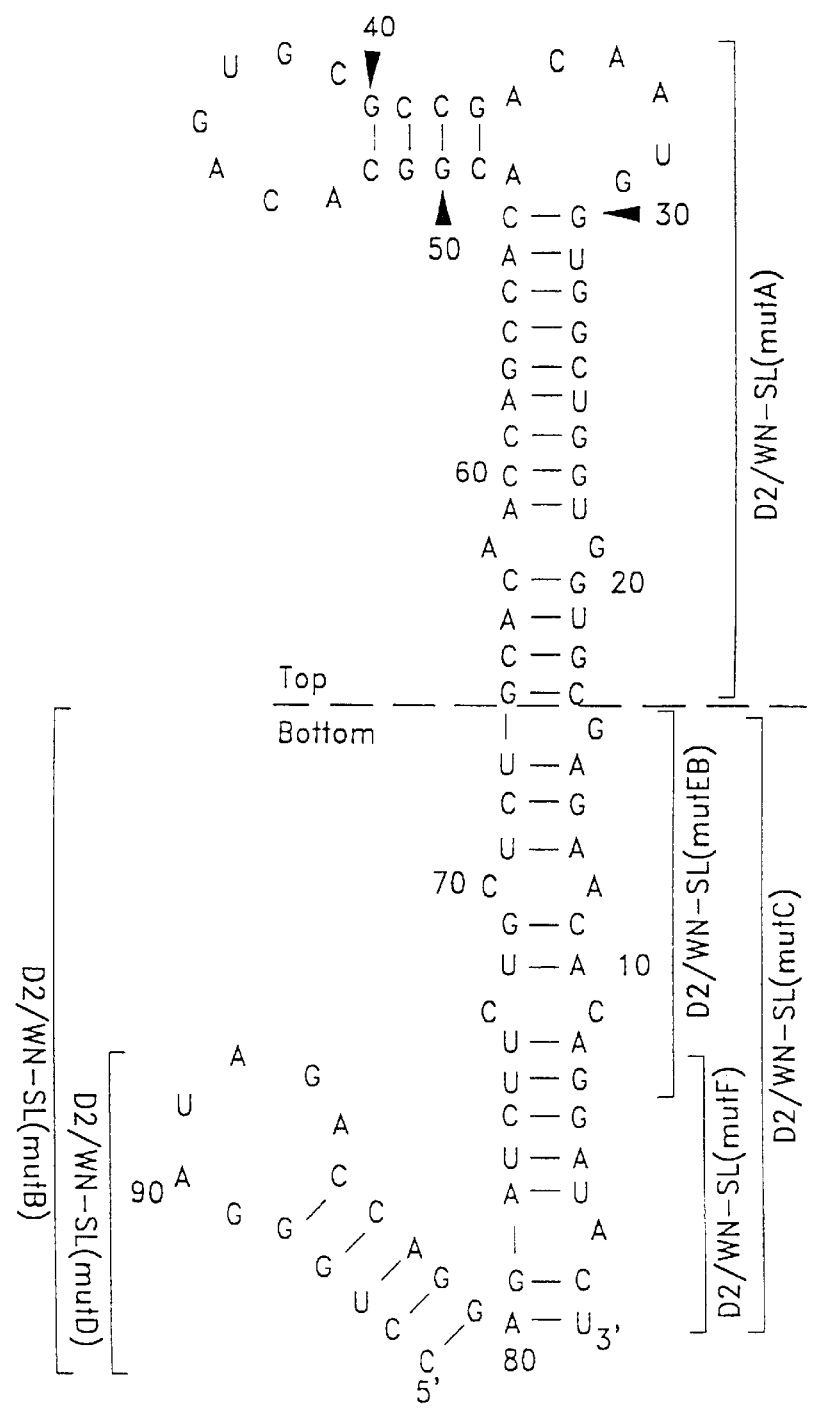

In dengue virus serotype 2 (DEN2), the predicted 3'-SL is formed by the 3'-terminal 93 nucleotides of the genome (FIG. 1). For West Nile virus (WN), it is formed by the 3'-terminal 96 nucleotide (FIG. 2). Ribonuclease probing confirmed the presence of the predicted 3'-SL in the WN genome and showed that interaction between the small loop and the lower portion of the adjacent long stem within the 3'-SL may result in a "pseudoknot" structure. Recent studies suggest a role for the 3'-SL in virus replication: (i) Three hamster kidney (BHK) cellular proteins were shown to bind specifically to an in-vitro synthesized RNA containing the WN 3'-SL nucleotide sequence; one of these cellular proteins was subsequently identified as translation elongation factor, eF1-α. It was proposed that the interaction of the 3'-SL with cellular proteins was related to initiation of negative-strand RNA synthesis. (ii) RNA transcripts representing the JE virus 3'-SL were shown to bind the JE virus NS5 protein in vitro; NS5 contains RNA-dependent RNA polymerase activity. (iii) In an in vivo study, an internal deletion of 3'-NCR nucleotide sequences extending downstream into the small stem and loop nucleotide sequence within the 3'-SL were lethal for DEN4 virus replication.

Although the 3'-SL structure in flavivirus RNA is well conserved among species, the involved primary nucleotide sequences are at best semi-conserved. Divergence of the nucleotide sequences is especially evident in the region of the long stem, while the nucleotide sequences of the loop segments are relatively well conserved (see for an example FIGS. 1, 2).

The present invention contemplates utility in generating mutant flaviviruses for use as vaccines effective against the corresponding flavivirus induced diseases. Any member of the family Flaviviridae containing a 3'-SL structure may be mutagenized according to the teachings of the present invention or with techniques known to those of skill in the art, to produce a replication-defective mutant virus that may be defective for replication in the relevant arthropod vector. The four serotypes of the dengue virus are contemplated as being particularly well suited for use in the present invention. Accordingly, in one embodiment mutations are made in the 3'-SL of dengue type 1. In another embodiment, mutations are made in the 3'-SL of dengue type 2. In still another embodiment, mutations are made in the 3'-SL of dengue type 3. And in yet another embodiment, mutations are made in the 3'-SL of dengue type 4.

The present invention contemplates the generation of flavivirus mutants that are replication-defective in their arthropod vector hosts for use as vaccines. Dengue virus mutants may be used as live, attenuated vaccines to induce immunological protection against dengue virus infection. To begin with, mutations in the DEN2 3'-SL were made. A full-length infectious cDNA clone of the DEN2 RNA genome was isolated. Mutations in the relevant nucleotide sequence of this cDNA were made according to the method of Polo, et al., "Infectious RNA transcripts from full-length dengue virus type 2 cDNA clones made in yeast," J. Virol. 71:5366–5374 (1997), hereby incorporated by reference. The nucleotide sequences of the WN 3'-SL were substituted for analogous nucleotide segments of the wild type DEN2 3'-SL, resulting in a series of DEN2/WN hybrid genomes. Additional mutants were constructed with transpositions of wild type DEN2 nucleotide sequences within the long stem of the 3'-SL region or an alteration of the wild type nucleotide sequence to abrogate formation of the long stem.

In one embodiment of the present invention nucleic acid substitutions were made to the 3'-SL structure of the dengue virus to limit the replicative ability of the virus in cultured host cells. In one embodiment, the 3'-SL structure was substituted with a suitable nucleic acid source. In this embodiment, the dengue virus sequence substituted may stretch from bases 1 to 93. In another embodiment the top portion of the 3'-SL structure of the dengue virus corresponding to bases 18 to 62 may be substituted with a suitable replacement sequence. In another embodiment the bottom portion of the 3'-SL structure the dengue virus sequence may be substituted and this region may stretch from bases 1 to 17 and from 63 to 93. In another embodiment, the bottom halve of the long stem portion of the 3'-SL structure of the dengue virus corresponding to bases 1–17 and 63–79 may be substituted. In still another embodiment, the small stem and loop portion of the 3'-SL structure of the dengue virus corresponding to bases 80–93 may be substituted. In yet another embodiment, the upper-most portion of the bottom half of the long stem portion of the 3'-SL structure of the dengue virus corresponding to bases 7–17 and 63–73 may be substituted. In again another embodiment, the lower-most portion of the bottom half of the long stem portion of the 3'-SL structure of the dengue virus corresponding to bases 1–7 and 73–79 may be substituted.

Suitable sequences for substitution in the 3'-SL region may be found in the viruses of the family Flaviviridae as these virus each possess a 3'-SL region. Flavivirus nucleic acid sequences are well known in the art and are readily available in the scientific literature. Representative viruses of family flaviviridae include: Powassan (GenBank accession no. L06436), Japanese encephalitis (GenBank accession nos. D90194, D90195, L48961, M18370, M55506, U14163, U15763), Central European encephalitis (TBE-W) (GenBank accession nos. U27491, U27493, U27495, U27496, U39292), Far Eastern encephalitis (TBE-FE) (U27490, U27492), West Nile (GenBank accession nos. M12294, L48977), yellow fever virus (GenBank accession nos. U52423, U52420, U52417, U52411, U52414, U52407, U52401, U52399, U52396, U52390, U21056, U21055, X02807, U17067, U17066), dengue virus type 1 (GenBank accession no. M87512), dengue virus type 2 (GenBank accession no. M29095, M19197, M20558, M84727, M84728), dengue virus type 3 (GenBank accession no. M93130), dengue virus type 4 (GenBank accession no. M14931), and Murray Valley encephalitis (GenBank accession nos. M35172, L48972, L48973, L48974, L48975, L48976).

The present invention contemplates mutant flaviviruses for use as vaccines that are deficient in replication in the vector stage of the viral life cycle, as compared to the wild type virus. The mutant flaviviruses are constructed and selected for the reduced ability to replicate in an invertebrate vector. Various mosquito species are known as flavivirus vectors. Representative mosquitoes include the genera Aedes, Culex, Anoplees, Mimomyia and Manosonia. Examples of particular species within the Aedes genus include: Ae. aegypti, Ae. albopictus, Ae. serratus, Ae. scapularis, Ae. niveus, Ae. furcifer, Ae. taylori, Ae. luteocephalus, Ae. opok, and Ae. africanus; and within the Culex genus comprise: C. tritaeniorhynchus, C. univittatus, C. tarsalis, C. nigripalpus, C. pipiens, and C. quinquefaciatus. Ae. aegypti, Ae. Albopictus are both known invertebrate vectors of the dengue virus. Various tick species are also known flavivirus vectors. Tick vectors from the genera Dermacenter, Haemaphysalis and Ixodes have all been implicated in various flavivirus diseases. Specific examples of tick species as flavivirus vectors include: *Ixodes ricinus*, and *Ixodes persulcatus*. Cells from any of these species of vectors may be isolated for testing a replication-defective flavivirus mutant in culture, and ultimately, in the field. The replicative ability of the mutant flaviviruses of the present invention determines the suitability of those mutant viruses for use as vaccines in that a reduced ability to replicate is a desirable feature in a live, attenuated vaccine stock.

The present invention further contemplates additional means to define replication-defective mutant flaviviruses. In one embodiment of the present invention the mutant flaviviruses contain mutations which result in a decrease in the generation of viral mRNA transcription such that viral mRNA is undetectable by standard slot-blot hybridization methods known in the art. In another embodiment, a mutant flavivirus is constructed where the mRNA species transcribed have a substantially reduced half-life in vivo and/or in vitro. In another embodiment, mutations in the 3'-SL of a mutant flavivirus genome result in a reduction in viral translation and thus a 10 to 100,000 fold (or 10 to 1000 fold) reduction in the amount of viral protein produced.

The present invention further contemplates using the number of virus particles produced by a replication-defective flavivirus to determine the suitability of that virus for use as a vaccine component. In one embodiment of the present invention, a suitable vector stage mutant flavivirus produces 10 to 100,000 fold (or 10 to 1000 fold) lower titers of viral particles than that of the wild type virus when grown in cultured arthropod vector cells. Ultimately, the replication-defective phenotype of the mutant flaviviruses must be stable in the live vector for a period of time of sufficient length to prevent the transmission of the virus vaccine to others.

Vaccines for providing immunological protection against flavivirus infection are contemplated. In one embodiment, vaccines for the protection against the flaviviral diseases of dengue fever or dengue hemorrhagic fever/shock syndrome caused by any of the serotypes of the dengue virus are provided by the present invention. Desirable vaccine compositions may include live, attenuated flaviviruses that have a mutation in the 3'-SL region of the flavivirus genome that results in a reduced ability to replicate in arthropod vectors.

One such vaccine contains a vector stage replication-defective dengue virus with a mutation in its 3'-SL region that reduces replication in adult *Ae. aegypti* and *Ae. albopictus* mosquitoes. This mutant dengue virus has been shown to have a markedly reduced ability to replicate in C6/36 cells, in the first 2–3 days after infection in *Ae. aegyptl*, and 3–5 days after injection in *Ae. albopictus*.

The vaccine compositions of the invention may desirably include a combination of mutant flaviviruses, for example, a mixture of the dengue virus mutants of the present invention. These mutant vaccine viruses may be directed against the various serotypes of the dengue virus. For example, in one formulation, the present invention provides a vaccine composition containing 3'-SL dengue virus mutants derived from the dengue virus serotypes 1, 2, 3 or 4. Suitable combination vaccines may contain serotype 2, or 2 and 3 or 2, 3 and 4 or 1, 2, 3, and 4. The present invention also contemplates any combination of the dengue virus serotypes that may be efficacious in preventing the spread of dengue virus caused disease. Combinations as any of the flaviviruses described herein for use as vaccines are also contemplated.

The vaccine compositions of the present invention may contain conventional carriers. Suitable carriers are well known to those of skill in the art. These vaccine compositions are preferably prepared in liquid unit dose forms. Other optional components, e.g., stabilizers, buffers, preservatives, excipients and the like may be readily selected by one of skill in the art. Alternatively, the vaccine compositions may be prepared in any manner appropriate for the chosen mode of administration, e.g., intramuscular administration, subcutaneous administration, intraperitoneal administration, etc. The preparation of a pharmaceutically acceptable vaccine, having due regard to pH, isotonicity, stability and the like, is within the skill of the art.

Optionally, the vaccine may be formulated to contain other active ingredients and/or immunizing antigens. For example, when adapted for intramuscular administration, formulation with a hepatitis B vaccine may be desirable.

The dosage regimen involved in a method for vaccination, including the timing, number and amounts of booster vaccines, will be determined considering various host and environmental factors, e.g., the age of the patient, time of administration and the geographical location and environment.

Also included in the present invention is a method of vaccinating humans against flavivirus infection with the novel mutant flaviviruses and vaccine compositions described above. For example, the vaccine compositions of the present invention may include one or more mutant dengue viruses described herein and administered by an intramuscular route, in a suitable dose, and in a liquid form.

The dosage for all routes of administration is generally greater than $10^3$, between $10^3$ and $10^9$ plaque forming units (pfu) of the mutant viruses. Additional doses of the vaccines may also be administered. It may be preferable to vaccinate susceptible individuals on an annual basis.

The following examples teach the generation of replication-defective mutant flaviviruses. These examples are illustrative and are not intended to limit the scope of the present invention. One of skill in the relevant art would be able to use the teachings described in the following examples to practice the full scope of the present invention.

EXAMPLE 1

Construction of Mutant Dengue Viruses

Production of DEN2 infectious cDNAs containing mutations in the 3'-SL. A full-length cDNA copy of a DEN2 genome (New Guinea C strain, hereinafter, "NGC") had previously been cloned into a yeast shuttle vector, pRS424. See Polo, et al. The recombinant plasmid was designated pRS424FLD2. We mutagenized the 3'-terminus of the cloned DEN2 genome by homologous recombination, according to a method previously described in Spencer, et al., "Targeted recombination-based cloning and manipulation of large DNA fragments in yeast," Methods Companion Methods Enzymol. 5:161–175 (1993), and hereby incorporated by reference. Briefly, plasmid pRS424FLD2, containing unique restriction sites Sac I and Apa I at the 3'-terminus and 181 nucleotides upstream from the 3'-terminus of the DEN2 sequence, respectively, was digested with these two enzymes. A 181 nucleotide fragment, including the nucleotide sequences encoding the wild type DEN2 3'-SL, was thus cleaved from pRS424FLD2 recombinant DNA. A PCR product which contained the desired mutations in the nucleotide sequence of the 3'-SL and which overlapped by 50 nucleotides the 5'- and 3-termini of the Sac I/Apa I digested recombinant plasmid was co-transformed with the linear Sac I/Apa I-digested DNA into *S. cerevesiae* strain YPH857 made competent using PEG according to the method of Valle & Wickner, "Elimination of L-A double-stranded RNA virus of *Saccharomyces cerevisiae* by expression of gag and gag-pol from an L-A cDNA clone," J. Virol. 67:2764–2771 (1993), and hereby incorporated by reference. After transformation, yeast were plated on tryptophan-minus (trp-) synthetic complete medium containing 2% agar and incubated at 30° C. for 3 days as described by Sherman, "Getting started with yeast," Methods Enzymol. 194:3–21 (1991), and hereby incorporated by reference.

Resultant isolated yeast colonies were transferred to 3 ml trp-liquid medium and cultured for 16–18 hours in a 30° C. shaker (250 rpm). Yeast were pelleted and resuspended, in 200 μl lysis buffer (1% Triton X-100, 1% SDS, 100 mM NaCl, 10 mM Tris-HCl, pH 8, and 1 mM EDTA) and 200 μl phenol: chloroform: isoamyl ethanol (25:24:1). The mixture was vortexed with 200 μl volume of 425- to 600-micron glass beads (Sigma; St. Louis, Mo.) for 10 minutes and then centrifuged for 2 minutes. The supernatant was precipitated in ethanol and resuspended in 50 μl of TE buffer. One microliter of the resulting suspension was used to transform 50 μl of *E. coli* STBL 2 competent cells (Life Technologies Inc.; Bethesda, Md.) to ampicillin resistance. After 3 days incubation at 30° C., colonies were cultured in 100 ml superbroth (BioWhitaker; Walkersville, Md.) with ampicillin (100 μg/ml) for 16 hours at the same temperature. Plasmid DNA was purified by Qiagen column tip-100 (Qiagen; Chatsworth, Calif.).

Construction of PCR products containing mutations in cDNA encoding the DEN2 3'-SL. To construct the PCR products used above to generate mutations of the DEN2 3'-SL, we utilized a BstY I site or a Hinf I site, 79 nucleotides and 15 nucleotides from the 3'-terminus of the DEN2 nucleotides sequence, respectively. Both of these sites lie within nucleotide sequences encoding the 3'-SL. PCR fragments extending up- and downstream from either of these sites were generated separately, digested with the appropriate endonuclease, then ligated together in vitro to form the required mutagenic fragment with sufficient overlap of adjacent sequences in pRS424FLD2 DNA. The ligated fragment was then amplified by PCR prior to co-transformation of yeast. All PCR products were generated using the same program for 30 cycles: 94° C. for 1 min/55° C. for 2 min/72° C. for 1 min. Native Pfu DNA polymerase (Stratagene, La Jolla, Calif.) was used in all PCR reactions.

PCR products containing mutations D2-SL(c), D2/WN-SL(mutD) and D21WNSL(mutE) were constructed in the following manner: To obtain the mutations located upstream of the BstY I site, genomic anti-sense primers encoding the BstY I site, the corresponding mutant nucleotide sequence, and 18 3'-terminal complementary nucleotides were used in PCR amplification together with a genomic sense primer 1 (5'-GCATGGCGTAGTGGACTAGCGG-3')(SEQ ID NO:1), which begins 242 nucleotides upstream from the DEN2 cDNA 3'-terminus. To obtain mutations located downstream of the BstY I site, genomic sense primers containing the BstY I site, the desired mutant nucleotide sequence, and 18 complementary nucleotides, were used in PCR amplification together with anti-sense primer 2 (5'-ATGATTACGCCAAGCGCGC-3') (SEQ ID NO:2) located 55 nucleotides downstream from the DEN2 cDNA 3'-terminus, within the pRS424 vector nucleotide sequence. Two hundred micrograms (200 $\mu$g) of each of the PCR products were digested with BstY I and gel purified, then the respective products representing sequences up and downstream from the BstY I site were ligated at room temperature for 16 hours. One microliter (1.0 $\mu$l) from this ligation reaction was used as template for further PCR amplification directed by primers 1 and 2. The final PCR products were ethanol precipitated prior to yeast transformation. In a similar manner, mutants D2/WN-SL(mutA), D2-SL(a), and D2-SL(b) were constructed using the Hinf I restriction site.

For mutants D2/WN-SL, D2/WN-SL(mutB), D2/WN-SL(mutC), and D2/WN-SL(mutF), each of the desired mutant fragments downstream from the BstY I site was first synthesized as a positive-sense 95 base pair oligonucleotide, including the last 80 nucleotides of either the DEN2 or the WN cDNA sequence and the 5'-proximal 15 nucleotides of the downstream pRS424 vector sequence. Next, a 50 base pair anti-sense oligonucleotide, complementary to vector DNA downstream from the 3'-terminus of the DEN2 cDNA and overlapping the positive-sense 95 base pair mutagenic oligonucleotide by 15 nucleotides at its 3'-terminus, was also synthesized. These pairs of oligonucleotides were annealed at the overlapping 15 nucleotide termini and extended by PCR to create 130 base pair mutant fragments representing the required nucleotide mutant sequences downstream from the BstY I site.

To generate revertants for the lethal and sublethal mutants D2/WN-SL, D2/WN-SL(mutB), D2/WN-SL(mutC), and D2/WN-SL(mutE), the corresponding wild type DEN2 3'-SL cDNA sequence was amplified by PCR using the recombinant plasmid pRS424FLD2 as template with primers 1 and 2. This PCR product was used for homologous recombination with each of the respective mutant recombinant cDNAs which had first been digested with Apa I and Sac I to remove the nucleotide segment containing the mutant 3'-SL.

To verify the presence of desired mutations in the context of the pRS424 recombinant plasmids used to generate infectious RNA, all PCR amplified regions were sequenced. Plasmids were also analyzed by restriction endonuclease digestion, using the enzymes EcoR I, Kpn I and Sac I in concert. Only recombinant plasmids that appeared to yield 9 fragments of the correct predicted sizes were used to generate RNA for transfection.

EXAMPLE 2

Confirmation of Mutant Structure and Function

RNA transcription, transfection of LLC-MK2 cells, and virus recovery. Wild type or 3'-SL mutant recombinant plasmid DNA (2 $\mu$g) was linearized by digestion with Sac I restriction endonuclease and used as template for RNA transcription catalyzed by SP6 RNA polymerase (Promega; Madison, Wis.), using an SP6 promoter that had been inserted upstream from the DEN2 cDNA insert in pRS424FLD2. RNA transcripts (0.5 $\mu$g) were transfected into a continuous line of monkey kidney cells (LLC-MK2) by electroporation. Briefly, RNA was added to LLC-MK2 cells ($10^6$) suspended in 300 $\mu$l phosphate-buffered saline (PBS). Cells and RNA were incubated on ice for 10 minute prior to electroporation at 200 V, 950 $\mu$F using a Gene Pulser 11 with a Capacitance Extender (BioRad; Hercules, Calif). Transfected cells were then plated in one 35-mm-diameter well of a 6-well tissue culture plate and fed with EMEM containing 10% fetal bovine serum.

Indirect Immunofluorescence Assay (IFA) to detect virus antigen production. IFA was performed on days 3 and 10 post-electroporation (p.e.) on cells that had been seeded to a 1-cm$^2$ chamber on a slide (LabTek; Naperville, Ill.) on the day of electroporation. In a second type of experiment involving IFA, a transfected cell monolayer (one 35-mm-diameter well of a 6-well plate) was trypsinized on days 5, 10, 15, and 20 p.e. On each of these days, $\frac{1}{20}$ of the total cells were transferred to a 1-cm$^2$ chamber slide and IFA was performed on this slide 16 hours later. The remaining cells were re-plated in fresh medium prior to the next time point in each instance. A 1:50 dilution in PBS of DEN2 hyperimmune mouse ascitic fluid (HMAF; American Type Culture Collection; Rockville, Md.) was used to detect viral antigens in acetone-fixed cells. Fluorescein-conjugated goat antimouse antibody (Kirkegaard and Perry Laboratories; Rockville, Md.) was used as a detector antibody at the same dilution. A Leitz Diaplan microscope fitted with a Leica/Wild MPS48 automated photographic system was used for all photomicrographs.

Virus growth curves and plaque morphology. Each of the supernatants derived from transfected LLC-MK2 cells was harvested when about 70% of cells were positive for viral antigens and passaged serially in a continuous line of Aedes albopictus sp. cells (C6/36 cells) at 30° C., or LLC-MK2 cells at 37° C. for mutant D2/WN-SL[mutF], in order to obtain sufficient titers of virus for further analysis. To determine plaque size, virus in media directly from transfected or from infected cells was serially diluted and used to infect LLC-MK2 cells in paired wells of 6-well plates. Plates were incubated at 37° C. for 8 or 20 days, then the monolayer was stained with neutral red for 16–18 hours. After staining, plaques were counted and plaque size was measured. To determine a virus growth curve, wild type DEN2 and each of the viable mutant viruses was used to infect both LLC-MK2 cells in 6-well plates and C6/36 cells in T25 flasks, at an m.o.i. of 0.01 in each case. Three hundred microliters (300 $\mu$l) of supernatant from infected cells was then harvested daily for 8 days. Virus titers for each day and each cell line were determined by plaque assay in LLC-MK2 cells by the method described above.

Verification of the sequences of the mutant viruses. Viable mutant viruses D2/WN-SL(mutA and mutF) and D2-SL(a)

and (b) were used to infect C6/36 cells (or LLC-MK2 cells in the case of mutant D2/WN-SL[mutF]) in a T-75 flask after 3 passages each in the respective substrates. When widespread CPE was observed (7–14 days), infected cell media were harvested and clarified by low-speed centrifugation. Then virus was precipitated with polyethylene glycol (PEG)-NaCl as described by Polo, et al. For D2/WN-SL (mutF), the pellet was resuspended in TNE (10 mM Tris-HCl, pH 8.0, 100 mM NaCl, 1 mM EDTA), and virus was further purified by pelleting through an 8.5 ml cushion of 10% glycerol in TNE at 35000 rpm in an SW40.1 Ti rotor for 4 hours at 4° C. RNA was prepared from virus or PEG pellets using the RNEasy™ kit (Qiagen). The 5'-cap structure on virion RNA was removed by incubation at 37° C. for 1 hour in a reaction containing 50 mM Na acetate, pH 6.0, 1 mM EDTA, 0.1% 2-mercaptoethanol 0.01% Triton X-100, 0.2 mM ATP, and 10–25 U tobacco acid pyrophosphatase (Epicentre Technologies; Madison, Wis.) in a final volume of 50 µl. After extraction with phenol-chloroform and ethanol precipitation, "de-capped" viral RNA was circularized by incubation overnight at 14° C. in a 100 µl reaction volume containing 33 mM Tris-acetate, pH 7.8, 66 mM K acetate, 10 mM Mg acetate, 0.5 mM dithiothreitol, 1 mM ATP, 10% dimethylsulfoxide, 200 U RNAsin (Promega; Madison, Wis.), and 25 U T4 RNA ligase (Epicentre Technologies; Madison, Wis.). Circular RNA was used as template for RT-PCR to amplify the joint containing the ligated 5' and 3' ends. The RT-PCR was primed with an oligonucleotide corresponding to anti-sense DEN2 nucleotides 172–155 and a sense primer corresponding to DEN2 nucleotides 10420–10437. Reaction conditions were essentially as described in Polo, et al., except that in some cases Expand polymerase (Boehringer-Mannheim, now Roche Molecular Biochemicals; Indianapolis, Ind.) was used instead of Pfu polymerase (Stratagene; La Jolla, Calif.) for PCR. Amplified products were sequenced using the anti-sense primer described above.

For mutants D2/WN-SL and D2/WN-SL(mutD), a RT-PCR product containing the 3'-SL nucleotides was derived by conventional methods from linear viral RNA, using a genomic anti-sense primer complementary to the expected 3'-terminal 18 nucleotides of WN RNA (for D2/WN-SL) or the 3'-terminal 23 nucleotides of DEN2 NGC RNA (for mutD) and a genomic sense primer representing DEN2 genomic nucleotide sequence upstream from the 3'-SL. D2/WN-SL RNA was prepared from total cellular RNA after TRIzol extraction, whereas D2/WN-SL(mutD) RNA was prepared from PEG-precipitated virus. The nucleotide sequences of all PCR products were obtained by an automated method (ABI Model 377 and an ABI Prism dye terminator cycle sequencing kit (ABI; Columbia, Md.).

Computer analysis of wild type and mutant 3'-SL nucleotide sequences. The predicted secondary structures of DEN2 and WN wild type 3'-SL nucleotide sequences and of the corresponding mutant nucleotide sequences were ascertained using the program DNAsis v2.0 on a Power Macintosh 9500 computer.

Viral protein and RNA studies. Pairs of 6-well plates containing confluent monolayers of LLC-MK2 cells were infected with wild type DEN2 or each of the mutant viruses, at an m.o.i. of 0.05. After two days, one such plate was starved for methionine and cysteine for 1 hour, then labeled with [$^{35}$S]-methionine plus [$^{35}$S]-cysteine at a concentration of 100 µCi/ml (>3000 Ci/mmol, Amersham) for 4 hours. Cells were lysed in RIPA buffer (150 mM NaCl, 100 mM Tris-HCl, pH 7.4, 1% Nonidet P-40, 1% sodium deoxycholate, 0.1% SDS), and DEN-specific proteins were immunoprecipitated with DEN2 HMAF at a 1:50 dilution. Immune complexes were collected on Pansorbin beads (Calbiochem; La Jolla, Calif.). Precipitated proteins were analyzed by electrophoresis on a 12% SDS-polyacrylamide gel using a tricine-based buffer system as described by Schagger & Von Jagow, "Tricine-sodium dodecyl sulfate-polyacrylamide gel electrophoresis," Anal. Biochem. 166:368–379 (1987), and hereby incorporated by reference. Total cellular RNA was prepared from the second plate of the pair, using TRIzol reagent. Viral RNA was detected and quantified by slot blot hybridization on Hybond-N nylon membrane (Amersham; Arlington Heights, Ill.), as suggested by the supplier. Briefly, RNA samples were denatured at 65° C. for 5 minutes with 50% formamide, 30% formaldehyde, and 1x MOPS buffer, then chilled on ice. 20x SSC was added to adjust the final concentration of the sample to 5x SSC. RNAs were applied to the nylon membrane and cross-linked to it using UV light. To generate the DEN2 cDNA probe, pRS424FLD2 DNA was digested with restriction enzymes Sph I and Stu 1, followed by gel purification of a product cDNA containing nucleotides 1379–7871 of the DEN2 sequence. This cDNA was radiolabeled with $^{32}$P-dCTP (Amersham; Arlington Heights, Ill.) to a specific activity of 108 cpm/µg DNA using the Prime-It kit (Stratagene; La Jolla, Calif.). Hybridization was performed at 500C for 16–18 hours in a buffer containing 5x SSC, salmon sperm DNA (100 µg/ml), 1% SDS, 1 mM EDTA and radiolabeled DNA probe (2×10$^5$ cpm).

EXAMPLE 3

Structure and Nucleic Acid Sequence Requirements for Denaue Virus Replication

To study the structural and nucleic acid sequence requirement for the 3'-SL for virus replication, a DEN2-WN chimeric genome was first constructed according the methods described in Example 1, starting from a full-length cDNA copy of the genome of a mouse-brain-adapted DEN2 virus cloned in a yeast shuttle vector, the recombinant plasmid pRS424FLD2. The chimeric genome was constructed by homologous recombination of cleaved pRS424FLD2 DNA with PCR product(s) containing the desired mutation, in yeast. The initial mutant construct (D2/WN-SL) contained the full-length wild type DEN2 sequence, except the last 96 nucleotides of the WN genome (the WN 3'-SL)(SEQ ID NO: 4) was substituted for the 3'-terminal 93 nucleotides of the DEN2 sequence (SEQ ID NO: 3), comprising the wild type DEN2 3'-SL (FIGS. 1, 2, and 3). The nucleotide sequence chosen to represent the WN 3'-SL had been determined from WN strain E101 viral RNA by Blackwell & Brinton, "Translation elongation factor-1 alpha interacts with the 3' stem-loop region of West Nile virus genomic RNA," J. Virol. 71:6433–6444 (1997).

In FIG. 3, the composition of the 3'-SLs in mutant viruses are depicted. The DEN2 nucleotide sequence is shown as a thin line, and the WN nucleotide sequence is shown as a thicker fine. In (A), mutant D2/WN-SL(mutA) contained a substitution of DEN2 nucleotides 18 to 62 (SEQ ID NO: 5) by WN nucleotides 17 to 66 (SEQ ID NO: 6), which comprised the top portion of the 3'-SL. In (B), mutant D2/WN-SL(mutB) contained a substitution of DEN2 nucleotides 1–17 (SEQ ID NO: 7) and 63–93 (SEQ ID NO: 8) by WN nucleotides 1–16 (SEQ ID NO: 9) and 67–96 (SEQ ID NO: 10), corresponding to the bottom portion of the 3'-SL. In (C), mutant D2/WN-SL(mutC) contained a substitution of DEN2 nucleotides 1–17 (SEQ ID NO: 7) and 63–79 (SEQ ID NO: 11) by WN nucleotides 1–16 (SEQ ID NO: 9) and 67–80 (SEQ ID NO: 12), corresponding to the bottom portion of the long stem. In (D), mutant D2/WN-SL(mutD) contained a substitution of DEN2 nucleotides 80–93 (SEQ ID NO: 13) by WN nucleotides 81–96 (SEQ ID NO: 14), corresponding the short stem and loop. In (E), mutant D2/WN-SL(mutE) contained a substitution of DEN2 nucleotides 7–17 (SEQ ID NO: 15) and 63–73 (SEQ ID NO: 16) by WN nucleotides 7–16 (SEQ ID NO: 17) and 67–75 (SEQ ID NO: 18). Finally, in (F), mutant D2/WN-SL(mutF) contained a substitution of DEN2 nucleotides 1–7 (SEQ ID NO: 19) and 73–79 (SEQ ID NO: 20) by WN nucleotides 1–7 (SEQ ID NO: 21) and 75–80 (SEQ ID NO: 22).

Initially, RNAs derived from transcription of the linearized DEN2 wild type and D2/WN-SL mutant recombinant plasmids were electroporated according to the method described in Example 2, into LLC-MK2 cells. The infectivity of mutant RNA compared to wild type RNA was assessed by IFA for DEN2 antigens in transfected cells, using murine anti-DEN2 antibodies, as described in Example 2. The D2/WN-SL chimera was negative for DEN2 antigens on day 3 (Table 1), and less than 10% of transfected cells were DEN2 antigen-positive by day 10. In contrast, DEN2 wild type RNA-transfected cells were positive for DEN2 antigens by IFA after 24 hours, and nearly 100% of cells in the monolayer were positive by day 6 or 7. Assuming that the efficiency of transfection of cells by wild type and mutant RNAs was approximately equal and that cells comprising the monolayer were homogeneous with respect to their ability to support virus replication, this result suggested that the D2/WN-SL mutant virus did replicate in the transfected cells but that replication was markedly impaired in comparison to that of wild type virus. Thus we interpreted the relatively late, delayed spread of positive fluorescence in the monolayer as evidence that progeny virions resulting from transfection were infectious. We termed this phenotype "sublethal."

TABLE 1

Properties of wt DEN2 and 3'-SL mutant viruses derived by transfection of LLC-MK2 cells.

| Virus | IFA[a] 3 days[b] | IFA[a] 10 days | Plaque size, mm (day)[c] |
|---|---|---|---|
| wt DEN2 | ++ | ++++ | 2.0 (8) |
| D2/WN-SL | − | + | 1.5 (20) |
| D2/WN-SL(mutA) | + | +++ | 2.0 (20) |
| D2/WN-SL(mutB) | − | − | NA |
| D2/WN-SL(mutC) | − | − | NA |
| D2/WN-SL(mutD) | + | ++ | 3.0 (20) |
| D2/WN-SL(mutE) | − | + | 1.5 (20) |
| D2/WN-SL(mutF) | + | ++ | 4.0 (20) |
| D2-SL(a) | + | +++ | 4.0 (20) |
| D2-SL(b) | + | ++ | 1.5 (20) |
| D2-SL(c) | − | − | NA |

[a]IFA, Indirect immunofluorescence assay. Cells were stained on day indicated with DEN2 HMAF (see Materials and Methods). Percentage of DEN antigen positive cells was determined by examination of at least 100 cells. (−), no positive cells; (+), <10% positive cells; (++), 10–40% positive cells; (+++), 40-70% positive cells; (++++), 70–100% positive cells.
[b]Days post-electroporation of LLC-MK2 cells. 0.5 µg of RNA was transfected into $10^6$ cells. On day 0, $10^5$ transfected cells were seeded to a 1 cm² chamber for IFA.
[c]Viable mutant viruses were passaged 3 times in C6/36 cells or in LLC-MK2 cells (D2/WN-SL[mutE]). The sequence of the 3'-terminal 242 nt in viral RNA was then verified, and the diameter of plaques was determined in LLC-MK2 cells. For all viable mutant viruses, plaques were not evident at day 8 post-infection. NA, not applicable; the mutation was lethal.

Because transfected cell monolayers did not always remain viable for sufficient periods of time to observe the growth of D2/WN-SL and other mutant viruses with the sublethal phenotype, a second type of assay for infectivity after transfection was performed. In FIG. 4, an indirect immunofluorescence assay (IFA) for growth of DEN2 wild type and DEN2-WN chimeric mutant viruses is shown. In this assay, $10^6$ LLC-MK2 cells were transfected by electroporation (see Example 2) with 500 ng of wild type or mutant viral RNAs that had been transcribed in vitro. Cells were then seeded to one 35-mm-diameter well of a 6-well tissue culture plate. On each of days 5, 10, 15, and 20 post-electroporation, the monolayer was disrupted by trypsinization, and 5% of the total cells were seeded to a cover slip for IFA. Remaining cells were re-cultured in fresh medium at each time point. DEN2 murine hyper-immune ascitic fluid was used in the assay at a 1:50 dilution to detect DEN2-antigen positive cells. Cells were fixed in acetone. See FIG. 3 for a graphical description of the mutant virus genotypes.

As seen in the FIG. 4, D2/WN-SL virus exhibited poor growth compared to wild type. Only about 40% of cells were positive by day 25. Thus the WN 3'-SL could not efficiently substitute for the DEN2 3'-SL to support DEN2 replication, despite the nearly identical predicted secondary structures of the two nucleotide sequences.

EXAMPLE 4

Chimeric Dennue Virus Mutants and Their Ability to Replicate

A series of DEN2-WN 3'-SL chimeric genomes were next constructed according to the methods described in Example 1, in order to determine which DEN2 nucleotide sequence elements within the 3'-SL were required for efficient virus replication. In this Example, specific regions of the DEN2 3'-SL were substituted for by the structurally analogous specific regions of the WN 3'-SL (FIG. 3). Initially, two such genomes were constructed, and their infectivity was assessed. D2/WN-SL(mutA) (FIG. 3A) contained a substitution of the "top" half of the DEN2 3'-SL (nucleotides 18–62 (SEQ ID NO: 5), numbering in the upstream direction from the 3'-terminal nucleotide of the genome; FIG. 1) with that of WN (nucleotides 17–66(SEQ ID NO: 6); FIG. 2). D2/WN-SL(mutB) contained the converse substitution (FIG. 3B); the "bottom" half of the DEN2 3'-SL sequence (nucleotides 1–17 (SEQ ID NO: 7) and nucleotides 63–93 (SEQ ID NO: 8)) was swapped for WN nucleotides 1–16 (SEQ ID NO: 9) and nucleotides 67–96(SEQ ID NO: 10), respectively. The bottom half of the WN 3'-SL alone and the analogous segment of the DEN2 3'-SL had previously been shown to contain the binding site for an unidentified 84-kDa BHK cell protein in vitro, whereas the bottom half plus the next 5 base pair of the top half of the WN structure were required to bind a specific $10^5$-kDa BHK cell protein (FIG. 2). The 50-kDa translation elongation factor, eF1-α, bound to a 3 nucleotide linear site in the top half of the WN long stem. One explanation for the decrease in viral replication seen as a result of the induced mutations is that mutations in the 3'-SL region of the virus may affect the binding of cellular proteins that are required for viral RNA transcription.

Following construction, these mutant dengue viruses where examined for functional activity by the methods described in Example 2. For D2/WN-SL(mutA), IFA was positive by day 3 after transfection of LLC-MK2 cells and 40% to 70% of cells were positive by day 10, when the monolayer was maintained continuously after transfection (Table 1). In the second IFA, when monolayers were re-seeded at 5-day intervals, cells became 100% antigen-positive by day 1, whereas wild type RNA transfected cells were 100% IFA-positive between days 5 and 10 (FIG. 4). Thus this mutant was "viable" but appeared to replicate less efficiently than wild type. In marked contrast, the mutation of the DEN2 genome in D2/WN-SL(mutB) was lethal; IFA for DEN2 antigens in transfected cells was negative, even after 25 days. This suggested that substitution of analogous WN 3'-SL nucleotide sequences was tolerated for the top half of the DEN2 3'-SL but that there was a specific requirement for DEN2 nucleotide sequences comprising the bottom half of the structure.

To define which portion of the DEN2 nucleotide sequence in the bottom half of the 3'-SL was absolutely required for viral replication, four additional mutants were generated according to the methods of Example 1. D2/WN-SL(mutC) contained the bottom half of the WN 3'-SL long stem in place of the analogous domain of the wild type DEN2 3'-SL (FIG. 3C); WN nucleotides 1–16 (SEQ ID NO: 9) and nucleotides 67–80 (SEQ ID NO: 12) replaced respectively DEN2 nucleotides 1–17 (SEQ ID NO: 7) and nucleotides 63–79(SEQ ID NO: 11) (FIGS. 1, 2). Thus DEN2 nucleotide sequence of the short stem and loop structure. Conversely, only the WN short stem and loop nucleotide sequence (WN nucleotides 81–96 (SEQ ID NO: 14)) was substituted for analogous DEN2 nucleotide sequences (DEN2 nucleotides 80–93 (SEQ ID NO: 13)) in D2/WN-SL(mutD) (FIG. 3D). Mutation D2/WN-SL(mutC) was lethal; IFA of the transfected LLC-MK2 cell monolayer for DEN2 antigens remained negative at all times post-electroporation up to 20 days. In contrast, mutant virus D2/WN-SL(mutD) replicated efficiently; a small percentage of cells were DEN2 antigen-positive by day 3 (Table 1), and essentially all cells were displaying viral antigen by day 20 in the discontinuous culture assay (FIG. 4). As for the other viable mutant viruses, replication of D2/WN-SL(mutD) was slightly less vigorous than that of wild type DEN2 virus, as judged by the spread of fluorescence in the transfected monolayer (Table 1, FIG. 4). Thus the incompatibility between WN and DEN2 nucleotide sequences in the hybrid 3'-SL structures appeared to be much more related to the presence of WN nucleotide sequences in the bottom half of the long stem than in the short stem and loop or in the top half of the long stem and loop.

Mutations D2/WN-SL(mutE) and D2/WN-SL(mutF) were next constructed according to the method of Example 1, to define which WN nucleotide sequences in the bottom half of the long stem were not compatible with efficient DEN2 virus replication (FIGS. 3E, 3F). D2/WN-SL(mutE) contained an 11 base pair substitution of the upper portion of the bottom of the long stem sequence, nucleotides 7–17 (SEQ ID NO: 15) and nucleotides 63–73 (SEQ ID NO: 16), by that of WN nucleotides 7–16 (SEQ ID NO: 17) and nucleotides 67–75 (SEQ ID NO: 18), whereas, in D2/WN-SL(mutF) the bottom portion of the same region of the long stem (nucleotides 1–7 (SEQ ID NO: 19) and nucleotides 73–79 (SEQ ID NO: 20)) was exchanged for the WN counterpart (nucleotides 1–7 (SEQ ID NO: 21) and 75–80 (SEQ ID NO: 22)).

Evaluating the functionality of the dengue mutants according to the methods of Example 2, the D2/WN-SL (mutE) mutation was sublethal; IFA was negative at day 3, and less than 10% of cells were positive on day 10 (Table 1). As assessed by the IFA on discontinuously cultured transfected cells (FIG. 4), replication of D2/WN-SL(mutE) virus could be seen to parallel that of the parent mutant, D2/WN-SL. Virus derived from construct D2/WN-SL(mutF) was obviously more viable; about 10% of cells were positive on day 3, and about 40% of cells were positive by day 10 (Table 1). Essentially all cells were positive by day 20 in the discontinuous culture assay (FIG. 4). Therefore, the DEN2 nucleotide sequence of the upper-most portion of the bottom half of the long stem in the 3'-SL was not dispensable for efficient virus replication; replacement of that segment by analogous WN nucleotide sequence was lethal or sublethal in all mutant constructs (FIGS. 3[top], 3B, 3C, 3E). In contrast, other DEN2 nucleotide sequences within the 3'-SL (FIGS. 3A, 3D, 3F) appeared to be exchangeable for analogous WN nucleotide sequences with much less significant loss of replication efficiency.

EXAMPLE 5

Additional Mutations of the Long Stem in the DEN2 3'-SL

Figure 5:
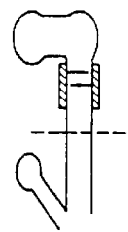
FIG. 5 shows a graphical representation of additional mutations made in the DEN2 3'-SL and their putative conformations. Transposed nucleotide sequences are indicated by cross-hatched rectangles.
Figure 5:
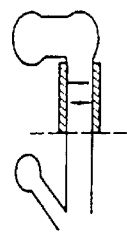
Figure 5:
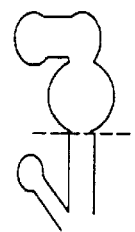

An additional group of mutants was constructed according to the methods of Example 1, to verify the suggestion that the conformation of the upper half of the long stem in the DEN2 3'-SL, rather than its nucleotide sequence, was of primary importance for virus replication. In mutant D2-SL (a), the wild type nucleotide sequences comprising the upper-most 6 base pair of the top half of the long stem were transposed (FIGS. 1, 5A). DEN2 nucleotides 24–29 (SEQ ID NO: 23) in the "right-hand" strand of the stem were substituted for by nucleotides 51–56 (SEQ ID NO: 24). Conversely, nucleotides 51–56 (SEQ ID NO: 24) in the "left-hand" strand were substituted for by nucleotides 24–29 (SEQ ID NO: 23). In mutant D2-SL(b), the 12 nucleotides complementary sequences of the right- and left-hand strands of the entire top half of the long stem (nucleotides 18–29 (SEQ ID NO: 25) and nucleotides 51–62 (SEQ ID NO: 26)) were similarly transposed (FIGS. 1, 5B). For both these mutants, only the positions of portions of the wild type long stem nucleotide sequence were altered; both constructs would be predicted to retain double-strandedness with identical free energy to that of the wild type DEN2 3'-SL In mutant D2-SL(c), base-pairing in the upper portion of the long stem was disrupted; nucleotides 18–29 (SEQ ID NO: 25) were substituted for by a repeat of the complementary sequence of the opposite strand, nucleotides 51–62 (SEQ ID NO: 26)(FIGS. 1, 5C). These predicted effects of mutations D2-SL (a, b, and c) on secondary structure of the 3'-SL were confirmed by the computer analysis method described in Example 2 of the respective mutant nucleotide sequences.

Figure 6:
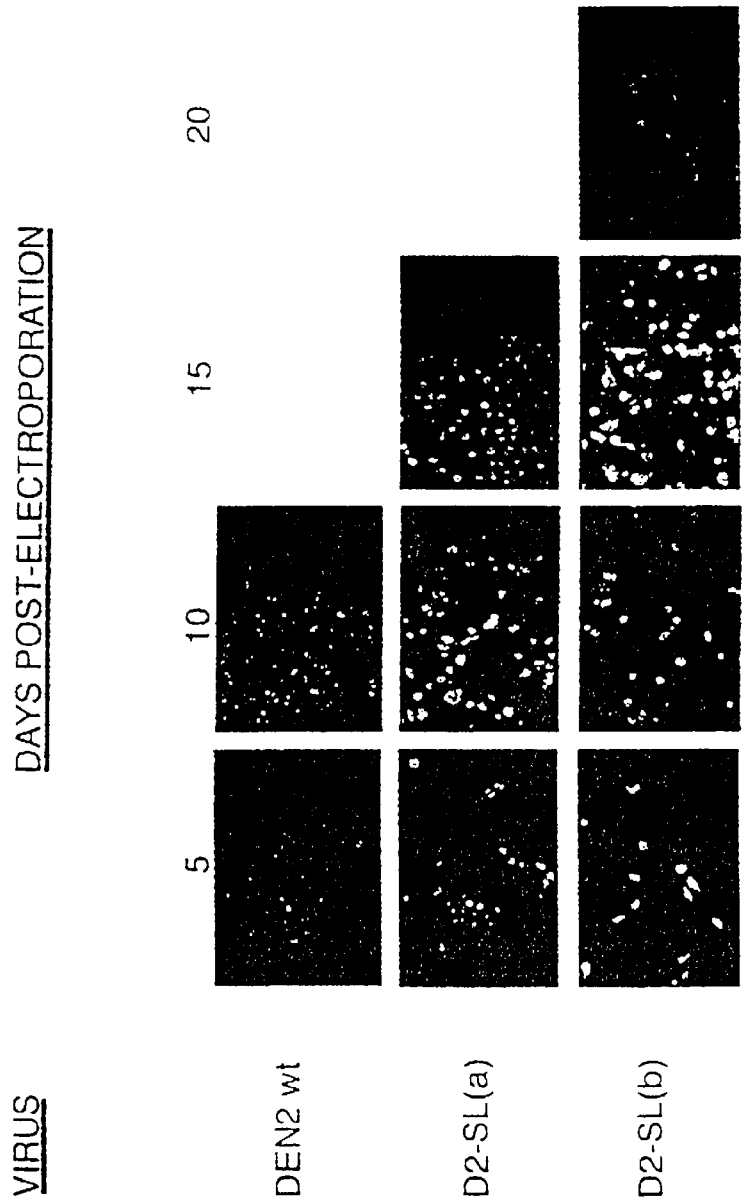
FIG. 6 shows photographs of an IFA for growth of DEN2 wild type and DEN2 3'-SL mutant viruses after transfection of LLC-MK2 cells.

Using the assay methods described in Examples 2 and 3, mutant RNAs D2-SL(a) and (b) yielded viable virus after electroporation into LLC-MK2 cells (Table 1). Both gave positive fluorescence in up to 10% of cells by 3 days. Cells transfected with mutant D2-SL(a) RNA were positive by IFA for DEN2 antigens in up to 70% of cells after 10 days and in essentially 100% of cells in the monolayer by day 15 in the discontinuous culture IFA (FIG. 6). For mutant D2-SL(b), IFA was positive in up to 40% of cells in 10 days and in nearly all cells by day 20 in the same assay. In contrast, mutation D2-SL(c) was lethal. No DEN2 antigen-producing cells were detected at any time after electroporation up to day 20. These results were consistent with those obtained for the DEN2-WN chimeric viruses: Re-positioning of wild type DEN2 nucleotide sequences within the top half of the long stem in the 3'-SL did not have severe effects on virus replication, as long as the double-strandedness of the structure was conserved. However, disruption of base-pairing in the top half of the long stem was lethal.

EXAMPLE 6

Kinetics of Replication of Mutant Viruses in LLC-MK2 and C6/36 Cells

Supernatant from cells electroporated with the "parent" mutant RNA, D2/WN-SL, was initially used to infect both LLC-MK2 cells and C6/36 cells. Both of these cell lines are permissive for WN and DEN2 replication. After incubation periods of up to 3 weeks, virus released into the medium was quantified by plaguing in LLC-MK2 monolayers. The highest titer achieved in medium from either cell line, even after several passages, was 60 pfu/ml. Therefore D2/WN-SL virus could not be included in the analysis of growth kinetics. For similar reasons, mutants D2/WN-SL(mutB, C, and E) were also excluded. The viable mutant viruses were passaged three times in C6/36 cells in order to obtain titers sufficient for determining growth curves, with the exception of the mutant D2/WN-SL(mutF), which replicated very poorly in C6/36 cells and was therefore passaged in LLC-MK2 cells prior to titration in both cell lines.

Figure 7:
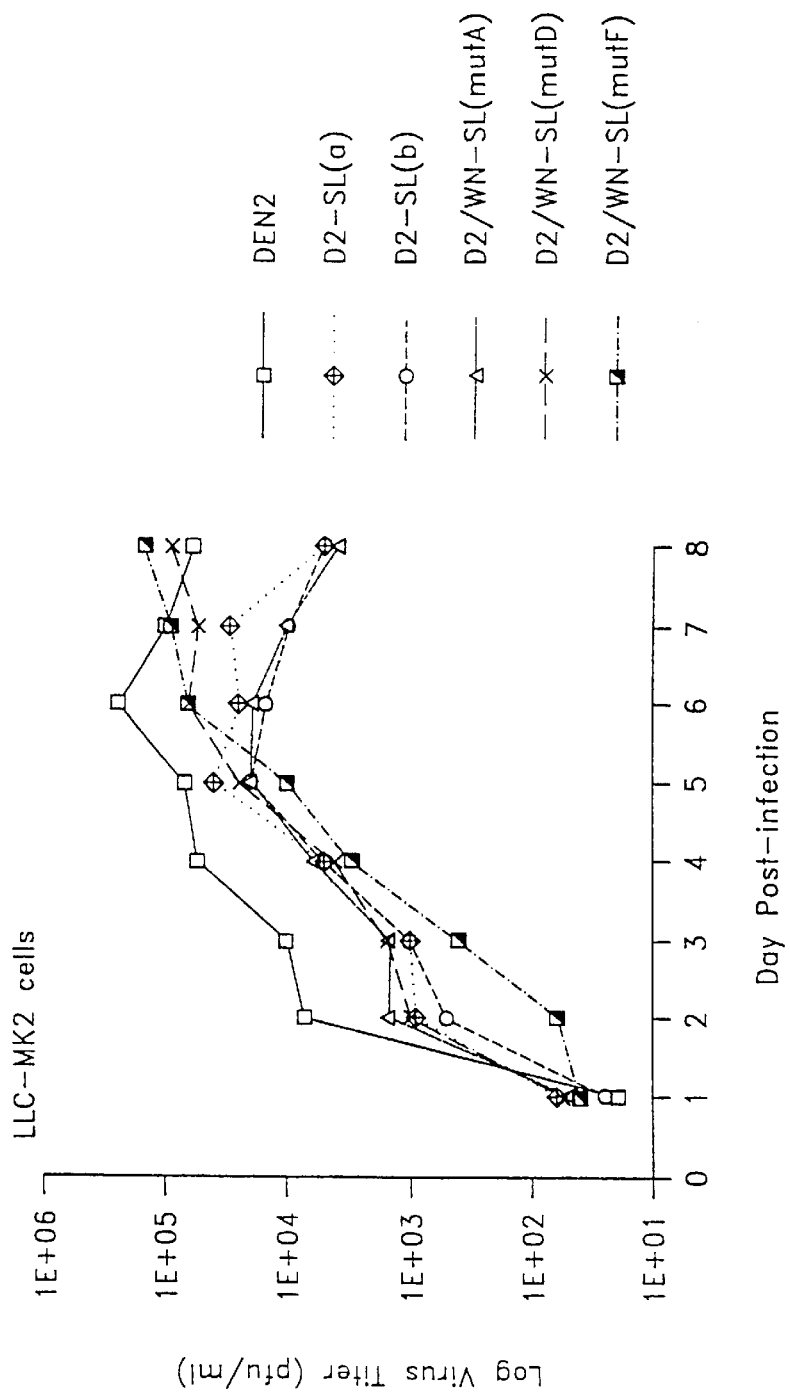
FIG. 7 shows growth curves for wild type and viable mutant DEN2 viruses where virus stocks were used to infect LLC-MK2 cells.

The growth rates of the viable viruses were determined in both LLC-MK2 and C6/36 cells. The supernatant of LLC-MK2 cells that had been transfected with in-vitro transcribed wild type and mutant DEN2 viral RNAs was used to infect C6/36 cells (or LLC-MK2 cells for mutant D2/WN-SL [mutF]), when the transfected cell monolayer was about 70% positive for DEN2 antigens by IFA. Wild type and viable mutant viruses were harvested and passaged three times in either of the substrates, then the 3'-terminal 242 nucleotide of each of the viral genomes were sequenced to confirm the stability of the respective mutations. Cells were infected with virus stocks of each of the mutants or wild type DEN2 at an m.o.i. of 0.01. Virus secreted into the medium was then titrated daily for 8 days. The peak titer for wild type DEN2 in LLC-MK2 cells was between $10^5$ and $10^6$ pfu/ml, achieved on day 6 post-infection (FIG. 7). Mutants D2-SL (a), D2-SL(b), and D2/WN-SL(mutA) were about 10-fold reduced in their peak titers compared to wild type on day 6. However, two of the mutants, D2/WN-SL(mutD) and D2/WN-SL(mutF), achieved titers of about $10^5$ pfu/ml by day 8 post-infection, nearly comparable to day-6 peak titers for wild type DEN2 (Table 2). We noted that titers of D2/WN-SL(mutF) were 100- to 1000-fold reduced compared to wild type on days 2 through 4 after infection (FIG. 7). This it was possible that this mutant further adapted to growth in LLC-MK2 cells during the course of the experiment by an occult mutation (in addition to that noted below). This seemed unlikely, however, since the virus had already been passaged 3 times in LLC-MK2 cells prior to the growth assay.

All viruses tested yielded higher titers in C6/36 than in LLC-MK2 cells, except D2/WN-SL(mutF) (Table 2). In addition, all mutant viruses were at least 10-fold reduced in peak titer compared to wild type DEN2 ($>10^7$ pfu/ml on days 3–5 (FIG. 8)). Mutants D2-SL(a) and D2/WN-SL (mutA) attained peak titers of $>10^6$ pfu/ml, and mutants D2-SL(b) and D2/WN-SL(mutD) attained peak titers of $>10^5$ pfu/ml. Peak titers for all mutant viruses were achieved from 1 to 3 days later after infection than for wild type virus. Surprisingly, D2-WN-SL(mutF) grew very poorly in C6/36 cells. Peak titer was $10^2$ pfu/ml on day 7, $10^5$-fold reduced compared to wild type in C6/36 cells. Whereas, this mutant grew at late times after infection to titers similar to that of wild type virus in LLC-MK2 cells. D2/WN-SL(mutF) virus was significantly specifically restricted for growth in C6/36 cells compared to all other viable mutant viruses.

TABLE 2

Peak titers of wt and viable chimeric mutant viruses in LLC-MK2 and C6/36 cells.[a]

| Virus[b] | Peak titer x $10^{-4}$ (day post-infection) | |
|---|---|---|
| | LLC-MK2 | C6/36 |
| DEN2 wt | >10 (6) | >1000 (3) |
| D2/WN-SL(mutA) | 1 (5) | >100 (4) |
| D2/WN-SL(mutD) | 10 (6–8) | >10 (5) |
| D2/WN-SL(mutF) | >10 (8) | $10^{-2}$ (7) |
| D2-SL(a) | >1 (5) | >100 (6) |
| D2-SL(b) | 1 (5) | >10 (5) |

[a]Data taken from results shown in FIGS. 6A and 6B.
[b]See FIGS. 2 and 4 for genotypes of mutant viruses.

EXAMPLE 7

Nucleotide Sequence Analysis of the Genomes of Viable Mutant Viruses and of Mutant D2/WN-SL Initially after 3 passages in C6/36 cells (or 3 passages in LLC-MK2 cells for D2/WN-SL[mutF]), the nucleotide sequence of the 3'-terminus of each viable mutant virus genome was wholly or partially verified. For mutants D2/WN-SL(mutA and mutF) and D2-SL(a) and (b), purified viral RNA was de-capped and circularized by ligation using T4 RNA ligase. Then RT-PCR was performed to derive a cDNA that spanned the 5'/3' junction of the viral RNA and included the entire 3'-SL nucleotide sequence, and these PCR products were sequenced.

By this analysis, mutant D2-SL(a) was shown to have sustained no spontaneous mutations within the 3'-SL during virus replication. However, mutant D2-SL(b) and D2/WN-SL(mutA) RNAs each contained an identical spontaneous mutation of nucleotide G5 to U, in the context of the DEN2 nucleotide sequence forming the bottom half of the 3'-SL in each of these mutant constructs (FIG. 1). This mutation had the effect of abrogating a G-C base pairing in the DEN2 long stem.

D2/WN-SL(mutF) RNA also contained a spontaneous point mutation, a deletion of nucleotide $A_3$ (see the WN 3'-SL nucleotide sequence, FIG. 2). This nucleotide is unpaired in the WN 3'-SL sequence determined by Blackwell and Brinton (FIG. 9A), and its deletion alters the 3'-terminal 7 nucleotide sequence of the mutF RNA from 3'-UCAUAGG (SEQ ID NO: 27) to 3'-UCUAGGC (SEQ ID NO: 28)(in which all nucleotides are hydrogen-bonded to the opposite strand of the long stem; FIG. 9B). For comparison, the wild type DEN2 3'-terminal 7 nucleotide sequence is 3'-UCUUGGA(SEQ ID NO: 19), where U4 is part of a U—U unbonded "bulge" in the long stem (FIGS. 1 and 9C). The two nucleotide differences in the 3'-SL of RNA from replicating mutF virus compared to that of wild type DEN2 RNA, A vs. U at nucleotide 4 and U vs. C at nucleotide 74 in the 3'-SL were apparently sufficient to abrogate replication, when mutF virus derived in monkey kidney cells was used to infect mosquito cells. This result raised the possibility that the lethal or sublethal phenotypes of mutants containing the bottom-most segment of the WN 3'-SL was related to the presence of nucleotide $A_3$ in genomic RNA. For mutant D2/WN-SL(mutD), no spontaneous mutations in the 3'-SL were detected by a technique that excluded sequence analysis of the 3'-terminal 23 nucleotides (see Example 2).

The sequencing procedure did not rule out that viable mutant viruses might have sustained additional spontaneous mutations upstream from the sequenced 3'-terminus. However, partial genomic nucleotide sequence upstream from the 3'-SL was obtained from D2/WN-SL virus RNA prepared 20 days after infection of LLC-MK2 cells, to determine whether spread of infection by this "sublethal" mutant virus at very late times after infection was related to the occurrence of a second-site mutation. No such mutation was detected within a domain that included the entire NS5 gene sequence, as well as the entire 3'-noncoding region (NCR) of the D2/WN-SL genome, except for the 3'-terminal 18 nucleotides.

EXAMPLE 8

Analyses of Plaque Morphology, Viral RNA and Protein Synthesis in Host Cell Lines Plaque morphology in LLC-MK2 cells. The size of plaques formed by the viruses bearing the sublethal mutations D2/WN-SL and D2/WN-SL(mutE) was assessed using virus harvested directly from transfected LLC-MK2 cells. Plaque size for the viable mutant viruses was assessed using virus passaged in C6/36 cells (or in LLC-MK2 cells for mutant D2/WN[mutF]), as well as virus derived directly from transfected cells. Wild type DEN2 virus produced plaques with a diameter of 2 mm after 8 days infection, while all the mutant viruses required 20 days to produce easily detectable plaques (Table 1). After 20 days, mutants D2/WN-SL(mutF) and D2-SL(a) produced 4-mm plaques. Mutants D2/WN-SL(mutA) and D2/WN-SL(mutD) produced 2- and 3-mm plaques, respectively, and mutants D2/WN-SL, D2/WN-SL(mutE) and D2-SL(b) produced plaques 1.5 mm in diameter. In general, plaque size correlated with results of IFA; viruses that were seen to spread cell-to-cell most rapidly by that assay also made the largest plaques, with the exception of the relatively small plaque size seen for mutant D2-SL(b). For the viable mutants, plaques formed by virus deriverd directly from transfection were not different in size from plaques formed by passaged virus.

Figure 8:
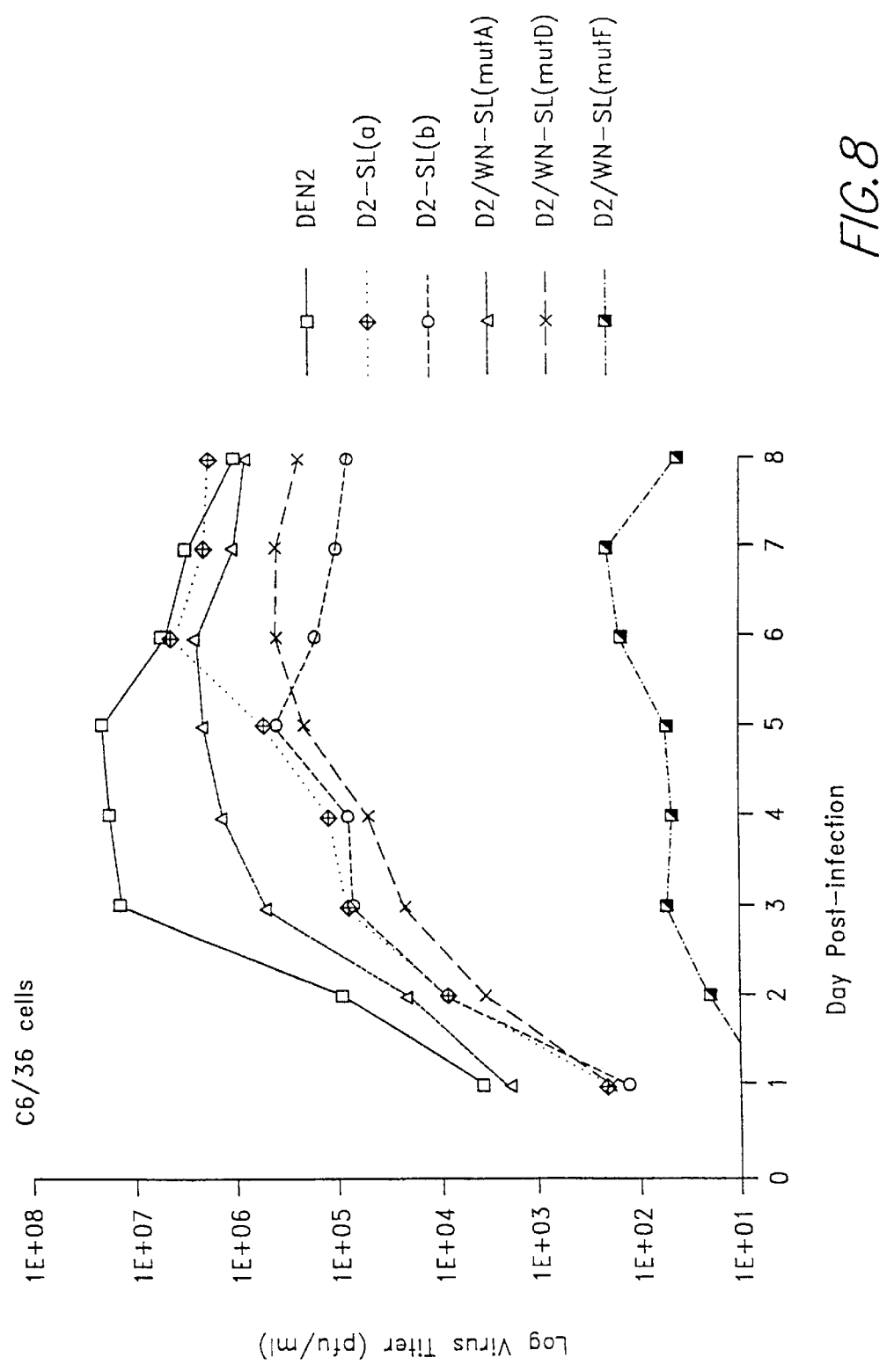

Analyses of viral RNA and protein synthesis. Viable mutants D2-SL(a), D2-SL(b), D2/WN-SL(mutA), D2/WN-SL(mutD), and D2/WN-SL(mutF) were used to infect monolayers of LLC-MK2 and C6/36 cells at an m.o.i. of 0.05. Total cellular RNA was extracted after 2 days. Slot-blot hybridization was performed using a $^{32}$P-dCTP-labeled DEN2 cDNA probe representing nucleotides 1379 to 7871 of the DEN2 nucleotide sequence. Since existing evidence suggests that subgenomic-sized RNAs are not produced during flavivirus replication, this assay was expected to detect all positive- and negative-sense DEN2 RNAs. The amount of viral RNA detected correlated with the titers of viruses in the growth curves at day 2 (FIG. 10; see also FIGS. 7, 8). Wild Type DEN2 viral RNA was more abundant than that of any of the mutant viruses in both cell lines. Viral RNA in D2/WN-SL(mutA)-infected cells was next most abundant, and the titer of this virus on day 2 was about 10-fold higher than for the other mutants, in both cell lines. As would be expected based on its growth characteristics, D2/WN-SL(mutF) RNA was least abundant of the viral RNAs in LLC-MK2 cells at day 2 and was undetectable in C6/36 cells using the hybridization methods described in Example 2. These data suggest that the decrease in viral replication observed in the mutant viruses may result from a defect in viral transcription rather than translation.

Figure 11:
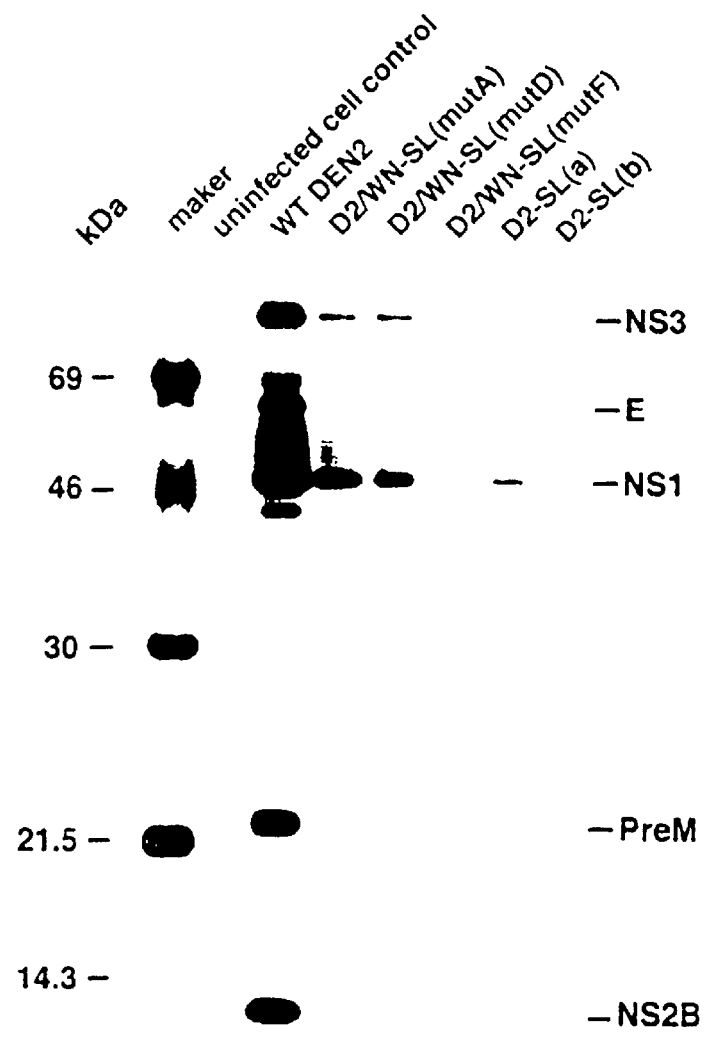

Viral protein synthesis in infected LLC-MK2 cells was also estimated (FIG. 11). For this experiment, viruses derived by transfection were passaged in C6/36 or LLC-MK2 cells, as described in Example 6. LLC-MK2 cells were then infected with these viruses at an m.o.i. of 0.05 and processed in parallel with cells used for the viral RNA analysis described above. Two days post-infection, cells were labeled for 4 hours with [$^{35}$S]-methionine and [$^{35}$S]-cysteine and then disrupted by trypsinization and lysed in RIPA buffer. Proteins in the lysate from one 35-mm-diameter well of a 6-well plate used to grow the cells were immunoprecipitated with DEN2 HMAF. Precipitates were collected using Pansorbin beads and analyzed in SDS-PAGE. Radiolabeled proteins were analyzed on a tricine-buffered 12% SDS-polyacrylamide gel. The DEN2 viral proteins prM, E, NS1, NS2B, and NS3 were then identified by size. Relative amounts of viral proteins detected paralleled amounts of viral, RNA detected at the chosen time point. Cells infected with mutant viruses yielded much less labeled viral protein than did cells infected with wild type DEN2. However, the ratios of each of the identifiable proteins were not obviously different for any of the mutants, as compared to wild type DEN2. In keeping with the results of the assay for virus-specific RNA, D2/WN-SL(mutF)-specific proteins were barely detectable on day 2, when the titer of this virus was 10- to 100-fold reduced compared to the other viable mutant viruses and to wild type (FIG. 7). Since there was a reasonable correlation between amounts of viral proteins and amounts of viral RNAs detected on day 2, we inferred that the defect(s) in replication of the mutant viruses were likely to be at the level of RNA synthesis, rather than at the level of translation. The assays for RNA and protein were repeated at day 4 after infection, with completely analogous results.

Flavivirus genomic RNAs contain 5'- and 3'-NCRs with lengths of approximately 100 and 400 to 600 nucleotides, respectively. The 3'-terminal 90 to 100 nucleotides of the 3'-NCR is predicted to form thermodynamically stable, adjacent stem-loop structures, collectively referred to here as the 3'-SL. (See Brinton, M. A., Replication of flaviviruses, p. 327–374. In, The Togaviridae and the Flaviviridae. Plenum Press, S. Schlesinger and M. Schlesinger led.) New York, N.Y. (1986); Brinton, et al., Virology 153:113–121 (1986)). Although the 3'-SL structure is conserved among flaviviruses, the primary nucleotides sequences in this region of the genome are quite heterogeneous. For example, the WN and DEN2 nucleotides sequences are only 37% homologous. However, higher levels of homology exist over localized areas within the 3'-SL, such as in the small stem-loop structure (FIGS. 1, 2).

Accumulated evidence suggests that the 3'-SL and an analogous conserved structure in the 5'-NCR play a crucial role in flavivirus replication. In vivo, deletions of 3'-NCR nucleotides sequences upstream from the 3'-SL in a DEN4 infectious cDNA were relatively well tolerated, whereas a deletion that extended into the nucleotides sequence required to form the small stem-loop structure in the 3'-SL was lethal for DEN4 replication. Men, et al., J. Virol. 70:3930–3937 (1996). In vitro, RNA transcripts containing all or only the "bottom" portion of the nucleotides sequence of the WN 3'-SL (FIG. 2), bound specifically to 56-, 84-, and 10$^5$-kDa proteins in uninfected BHK cellular extracts, and the "56-kDa" protein was subsequently identified as the 50-kDa translation elongation factor, eF1-α. Blackwell & Brinton, J. Virol. 69:5650–5658 (1996); Blackwell & Brinton, J. Virol. 71:6433–6444 (1997). Binding of eF1-α to the WN 3'-SL was dependent upon its phosphorylation. Another recent study showed that the 3'-terminal 83 nucleotides of the Japanese encephalitis virus (JE) genome (the long stem and loop within the 3'-SL) could compete with full-length JE RNA for binding to the viral RNA-dependent RNA polymerase, NS5, and that longer portions of 3'-terminal sequences also bound the virus-coded helicase, NS3, to form a "replication complex". Chen, et al., J. Virol. 71:3466–3473 (1997); see also, Tan, et al., Virology 216:317–325 (1996). Preliminary data from another study suggested a requirement for the flavivirus 3'-SL in translation. Li, & Brinton, Abstracts of the American Society for Virology 15th annual meeting. W2-1; p.85 (1996). Stable stem and loop secondary structures at the 5'- and 3'-termini of rubella virus genome RNA bound La protein and calreticulin, respectively. Atreya, et al., J. Virol. 68:3848–3851 (1995); Pogue, et al., J. Virol. 70:6269–6277 (1996). Phosphorylation-dependent binding of the rubella 3'-SL by calreticulin was linked to initiation of negative-strand RNA synthesis and to an effect of virus infection on arrest of the cell cycle.

Study of the binding of the WN 3'-SL by eF1-α and studies of binding of other cellular proteins to viral RNA secondary structures support the proposition that highly specific nucleotides sequence elements within such structures may be important for binding of regulatory proteins. Bartel, et al., Cell 17:529–536 (1991); Blackwell & Brinton, J. Virol. 69:5650–5658 (1996); Blackwell & Brinton, J. Virol. 71:6433–6444 (1997). Experiments described here were designed to study the structural and nucleotides sequence requirements for the 3'-SL in vivo in the context of the replication of DEN2 virus. The chimeric virus D2/WN-SL, which contained the 96-nucleotides sequence of the WN 3'-SL as a substitute for the 93-nucleotide sequence of the DEN2 3'-SL, was greatly impaired for viral replication. This defect could occur by two mechanisms: (i) Some essential RNA—RNA or protein-RNA interaction is reduced in efficiency or abrogated for the majority of transfected molecules; virus replication occurs at a normal rate from a reduced number of substrate genomes in a reduced number of cells, or (ii) replication of all transfected genomes occurs at a slower than normal rate in all transfected cells, due to a series of impaired interactions that must occur at successive points in the replication process. In either case, the 3'-SL conformation alone was not sufficient to support replication; specific DEN2nucleotides sequence elements within the 3'-SL were required for interaction either with viral proteins or with other regions of the viral genome. Possibly, specific nucleotides sequences of the DEN2 3'-SL are required to bind the DEN2 NS5 and/or NS3 to form the putative replication complex recently described for JE or to interact with specific sequence(s) in the DEN2 5'-NCR. Chen, et al., J. Virol. 71:3466–3473 (1997). It seemed less likely that the defect in replication was related to reduction in binding of cellular proteins by the 3'-SL, assuming that the DEN2 3'-SL binds the same set of proteins as does the WN 3'-SL Truncated DEN3 3'-SL RNAs efficiently competed with analogous WN 3'-SL segments for binding of two (as yet unidentified) BHK cell proteins of the three specifically bound by the WN sequence (the 84- and $10^5$-kDa species), and the DEN2 3'-SL long stem contains an nucleotides sequence (C62-U63-C64; FIG. 1) in a position analogous to that shown to be the major binding site for the third 3'-SL binding protein, eF1-α, in the WN 3'-SL (C63-A64-C65; FIG. 1). The phenotype was probably not due to the accidental introduction of other occult mutations into the DEN2 genome during the mutagenesis procedure, since this and all other "lethal" and "sublethal" mutations (see below) could be rescued by replacement of the respective chimeric 3'-SL structures with the wt DEN2 3'-SL nucleotides sequence.

Next mutant DEN2 cDNAs were constructed in which various segments of the DEN2 3'-SL were substituted by analogous segments within the WN 3'-SL to determine which elements of the DEN2 nucleotides sequence in the 3'-SL were required for efficient virus replication. We defined "top" and "bottom" portions of the DEN2 and WN 3'-SL structures, since information regarding the in vitro cell protein-binding properties of the bottom portion of the WN 3'-SL had previously been defined. We also constructed a set of mutations in the context of the "all-DEN2" 3'-SL. All of the D2/WN substitution-mutant 3'-SL nucleotides sequences and the all-DEN2 mutants (a) and (b) were predicted by computer analysis to form 3'-SL structures in which base-pairing predicted for the wt parental 3'-SLs was preserved, allowing us to infer that modulation of the efficiency of replication of mutant viruses with respect to wt was largely due to alterations of the wt DEN2 nucleotides sequence comprising the 3'-SL.

Phenotypes of the mutant viruses fell into 3 categories: (1) Viable, but slightly impaired for replication in LLC-MK2 and/or C6/36 cells compared to DEN2 wt. Cells transfected with these mutant RNAs were typically negative for IFA for DEN virus antigens at 24 hours after transfection (in contrast to cells transfeited with wt RNA) but positive after 3 days. Analysis of viral RNA and protein synthesis for wt compared to viable mutant viruses showed no obvious lesion at the level of translation, and we inferred that viable mutants were more or less defective compared to wt, at the level of RNA replication. (2) Sublethal. IFA for DEN2 antigens was negative at 3 days and positive by day 10 after transfection. Spread of IFA-positivity in the transfected monolayer indicated that infectious virus was produced. However, growth curves for these mutants in LLC-MK2 cells and C6/36 cells could not be obtained. The "parent" mutant. D2/WN-SL, was in this category. (3) Lethal. IFA of the transfected monolayer for DEN2 antigens remained negative at all times up to 25 days.

Three of the DEN2-WN chimeric substitution mutations, D2/WN-SL(mutsB, C, and E; see FIG. 3) were lethal or sublethal for DEN2 replication. Each of these constructs contained substitution mutations involving all or part of the bottom half of the long stem. Mutations D2/WN-SL(mutB) and D2/WN-SL(mutC), which substituted the entire bottom half of the WN 3'-SL, or only the bottom half of the long stem within the WN 3'-SL, for the respective analogous DEN2 nucleotides sequences, were lethal. D2/WN-SL (mutE) contained the most minimal exchange of DEN2 for WN nucleotides sequences, involving only the upper-most portion of the bottom half of the long stem and had the sublethal phenotype of the parent mutant, D2/WN-SL. This result suggested that DEN2 nucleotides 7–17 (SEQ ID NO: 15) and 63–73 (SEQ ID NO: 16) were required for the "viable" phenotype of mutant viruses. However, the present data do not permit a simple explanation of the finding that some of the mutations involving the bottom half of the long stem were sublethal and some were lethal. We speculate that the two lethal mutations (D2/WN-SL[mutB and C]) must have induced an additional defect in RNA replication or translation that was not conferred by the sublethal mutations D2WN-SL or in D2/WN-SL(mutE), related to the specific composition of the respective chimeric 3'-SL nucleotides sequences. For example, in the lethal mutations, the bottom-most 7-base pair segment of the long stem was derived from the WN nucleotides sequence, and the entire "top" of the long stem was derived from the DEN2 nucleotides sequence. Whereas, for the sublethal mutations those respective nucleotides sequences in the 3'-SL were derived either entirely from the WN sequence (D2/WN-SL) or entirely from the DEN2 sequence (D2/WN-SL[mutE]), Mutant D2/WN-SL(mutA) contained the entire top portion of the WN 3'-SL, and the virus replicated efficiently, to only about a 10-fold lower peak titer than did DEN2 wt in both LLC-MK2 and C6/36 cells. Since the nucleotides sequence of the top half of the WN 3'-SL diverges from that of the DEN2 3'-SL, the viability of the mutant suggested that conformation of this domain, rather than its primary nucleotides sequence, was the more critical factor for virus replication. As a second test of this hypothesis, we constructed additional mutations of the top half of the 3'-SL in an "all-DEN2" context (see FIG. 5). In two of these mutants, part (D2-SL[a]) or all (D2-SL[b]) of the nucleotides sequences comprising the complementary strands of the top half of the long stem were transposed, thus repositioning the respective nucleotides sequence elements in the DEN2 3'-SL, while not altering its predicted stability compared to wild type. In the third mutant, D2-SL(c), double-strandedness of the top half of the long stem was completely disrupted by substitution of the nucleotides sequence of one strand with a repeat of the nucleotides sequence of its opposite strand. Mutations D2-SL(a) and D2-SL(b) yielded viable virus in both cell lines, whereas mutation D2-SL(c) had the lethal phenotype. Thus the conformation of the top half of the 3'-SL, rather than its primary nucleotides sequence was the more critical factor for viability.

Mutants that contained substitutions of WN nucleotides sequences for DEN2 nucleotides sequences in the small stem and loop (D2/WN-SL[mutD]) and in the bottom-most portion of the long stem (D2/WN-SL[mutF]) also were viable. The homology between the DEN2 and WN 3'-SL nucleotides sequences is greatest in the small stem and loop domain: The 6 nucleotides that comprise the loop region (FIGS. 1, 2), the sequences 5'-GAAAGA-3' for DEN2 (nucleotides 89–84) and 5'-GAUAGA-3' for WN (nucleotides 91–86) differ by only one nucleotides, and the stem of the WN structure is longer than that of DEN2 by one G-C base pair. Shi et al have suggested that the first 4 of the 6 nucleotides of the WN small loop sequence may form a pseudoknot by hydrogen bonding with nucleotides 71–74 in the adjacent long stem, and a similar structure in poliovirus genomic RNA has been implicated in RNA amplification. Shi, et al., Biochemistry 35:4222–4230 (1996); Jacobson, et al., J. Virol. 67:2961–2971 (1993). Inspection of the nucleotides sequence of the long stem for DEN2 suggests that formation of a pseudoknot might also be possible for the chimeric structure formed by D2/WN(mutD) RNA.

Replication-competent D2/WN-SL(mutF) virus derived in LLC-MK2 cells was shown to contain a spontaneous deletion mutation within the substituted WN segment of the 3'-SL (see FIG. 9). The 3'-SL of the resultant mutan genome thus resembled that of wt DEN2 more closely than did the original mutF construction, save for a U to C change in mutF RNA vs wild type DEN2 RNA at nucleotides-74 and the absence in the mutant genome of a "bulge" in the long stem created by the alignment of $U_4$ with $U_{76}$ in the wild type DEN2 sequence (FIG. 9). This difference between the mutant genome and the wt nucleotides sequence apparently accounted for the observed failure of mutF virus to replicate in C6/36 cells. Spontaneous deletion of WN nucleotides $A_3$ in replicating mutF viral RNA may provide a clue to the lethal or sublethal phenotypes of other mutants that contained the bottom-most portion of the WN 3'-SL; failure of those mutants to replicate efficiently in monkey cells may have been related to a deleterious effect of nucleotides $A_3$ on DEN2 replication.

D2/WN(mutF) virus was uniquely defective with regard to its host cell-specific interactions, a phenotype that could be related to binding of cellular proteins to the 3'-SL. For example, mosquito cell proteins putatively required for binding to the 3'-SL may have different binding specificities from the analogous mammalian cell proteins. A similar one was advanced to explain the phenotypes of Sindbis virus host range mutants with deletions in the 5'- or 3'-NCR. Kuhn, et al., J. Virol. 66:7121–7127 (1992). Also, a DEN4 host range mutant that had sustained a 6-nucleotides deletion in the 5'-NCR was similarly restricted for growth in mosquito cells but grew well in monkey kidney cells. Cahour, et al., Virology 207:68–76 (1995). The complement of the genomic 5'-NCR, the 3'-NCR in negative-standard flavivirus RNA, is also predicted to form a stable stem-loop structure and also binds specific cellular proteins. Shi, et al., J. Virol. 70:6278–6287 (1996). It is possible that positive- and negative-strand RNA synthesis may in part be regulated by the analogous interactions of the two different stem-loop structures with cellular proteins, as others have suggested. This characteristics of this mutant dengue virus are further studied in Example 9.

EXAMPLE 9

Replication Efficiency of D2/WN-SL(mutF) in Two Species of Aedes Mosquito

The only known vectors for the transmission of dengue virus to man are Ae. aegypti and the Ae. albopictus species. Interestingly, the D2/WN-SL(mutF) failed to replicate in cultured mosquito cells (the C6/36 cell line, derived from Ae. albopictus larvae). This inability to replicate in mosquito cells is a desired property of a dengue virus vaccine.

The replication characteristics of this replication-defective dengue virus mutant in adult mosquitoes was further studied to establish its utility as a dengue virus vaccine. Accordingly, adult mosquitoes, 5 per time point, were inoculated trans-thoracically with 0.25 microliters of either wild type or D2/WN-SL(mutF) virus at comparable titers of between 3 and 5 log pfu/ml. At the time points shown, groups of five mosquitoes were separately emulsified, and virus in each preparation was eluted in Eagle's Minimal Medium (EMEM) containing glutamine and 10% fetal bovine serum, serially diluted in medium, and used as inoculum for a confluent monolayer of LLC-MK2 cells, also maintained in 10% EMEM. After about 7 days incubation, plaques formed in the LLC-MK2 monolayers were counted. Titers are given in the standard form of "$\log_{10}$ pfu/ml." Table 3 shows the titers of D2/WN-SL(mutF) virus or wild type DEN2 virus in adult mosquitoes harvested at days 2, 4, and 7 after infection.

TABLE 3

Replication of D2/WN-SL(mutF) Virus in Adult Mosquitoes Compared to cDNA-derived Wild Type Parent DEN2 NGC Virus

| Species | virus[a] | Days after inoculation[b] | | |
|---|---|---|---|---|
| | | 2 | 4 | 7 |
| Ae. aegypti | parent | 3.3 | 3.8 | 4.9 |
| | mutant | 1.6 | 3.9 | 5.1 |
| Ae. albopictus | parent | 2.9 | ≈5 | 5.5 |
| | mutant | 0.3 | 0.3 | 3.2 |

[a]Wild type DEN2, 4.1 $\log_{10}$ pfu/ml of clone 3-3 cDNA-derived DEN2 NGC virus; D2/WN-SL(mutF), 4.6 $\log_{10}$ pfu/ml of cDNA-derived D2(WN-SL(mutF) virus.
[b]Mosquitoes were infected by intra-thoracic injection on day 0 with 0.25 μl virus suspension. At indicated points, mosquitoes were emulsified in buffer and virus was titered by plaque count in LLC-MK2 cells. Results are the average titer of virus from 5 mosquitoes per time point. Titers given in $\log_{10}$ pfu/ml.

The data in Table 3 shows that the mutant dengue virus D2/WN-SL(mutF) was replication-defective in both Ae. aegypti and Ae. albopictus. When replicating in Ae. aegypti, D2/WN-SL(mutF) was found to produce about a 40-fold lower titer of virus than that of the parent virus at time point day 2. The data in Ae. albopictus was even more striking. At days 2 and 4, D2/WN-SL(mutF) virus could not be detected, (0.3 is the lower limit of the assay) data show that the nature of the mutation contained in D2/WN-SL(mutF) limits the replicative capabilities of this mutant in live mosquitoes. Further, while it appears that the mutation undergoes a reversion in adult mosquitoes, that reversion occurs 48 hours after the vector is inoculated with the replication-defective mutant virus for Ae. aegypti and only after seven days for Ae. albopictus. Either period is longer than the interval between feedings for the vector. Therefore, a human bitten by a mosquito carrying the mutant virus is unlikely to become infected with that virus due to the mosquito. The replication defect in the virus thus prevents or reduces the likelihood of transmission of that virus to subsequent humans who encounter the virus-carrying mosquito.

EXAMPLE 10

Method of Making a Flavivirus Virus Vaccine

Replication-defective flaviviruses are engineered in the manner described in the previous Examples. For example, the present invention contemplates a method to produce replication-defective dengue viruses suitable for use in a dengue virus vaccine composition. An example of such a virus is dengue type 2 D2/WN-SL(mutF), and its suitability for use as a vaccine arises from its reduced ability to replicate in mosquito cells and live mosquitoes. Candidate mutant dengue virus strains to be used as vaccines will be generated and will have been shown to be replication-defective in mosquito cells and live mosquitoes. These candidate viruses will be grown in a permissive cell line so as to produce a sufficient quantity of virus to permit the formulation of a vaccine.

EXAMPLE 11

Method of Making a Dengue Type 1 Virus Vaccine

A replication-defective dengue type 1 virus will be engineered in the manner described in the previous Examples and manufactured into a vaccine according to Example 10.

EXAMPLE 12

Method of Making a Dengue Type 3 Virus Vaccine

A replication-defective dengue type 3 virus will be engineered in the manner described in the previous Examples and manufactured into a vaccine according to Example 10.

EXAMPLE 13

Method of Making a Dengue Type 4 Virus Vaccine

A replication-defective dengue type 4 virus will be engineered in the manner described in the previous Examples and manufactured into a vaccine according to Example 10.

EXAMPLE 14

Method of Making a Yellow Fever Virus Vaccine

A replication-defective yellow fever virus will be engineered in the manner described in the previous Examples and manufactured into a vaccine according to Example 10.

EXAMPLE 15

Testing of Attenuated Flavivirus Vaccines in Primates

Subhuman primate, but not other animals, are readily infected with dengue virus by the peripheral route (Simmons, et al., Philipp. *J. Sci.* 44:1–247 and Rosen, *Am. J. Trop. Med. Hyg.* 7:406–410, 1958). Infection of monkeys represents the closest experimental system to dengue virus infection of humans. The response of rhesus monkeys to dengue infection is similar to that of humans in that there is a four to six day viremia, although lower primates do not develop clinical dengue symptoms. The objectives of dengue or other flavivirus studies in monkeys are: (1) to evaluate the immunogenicity of various candidate vaccines; (2) to evaluate the infectivity and virulence of candidate dengue virus vaccines as measured by the duration of viremia in days and the peak virus titer in pfu/ml; and (3) to evaluate the efficacy of the above-mentioned vaccines to protect animals against challenge by attenuated dengue virus.

(1) Inoculation: Groups of rhesus monkeys are inoculated with a series of dilutions of virus diluted in Eagle's minimal essential medium/0.025% human serum albumin.

(2) Blood collection: Following inoculation of attenuated dengue virus, blood sample of 3.0 ml are taken daily for two weeks and 5.0 ml at 3 weeks, 4 weeks, 6 weeks and 8 weeks.

(3) Challenge dengue virus or other flavivirus: Where virus challenge is deemed appropriate to evaluate the protective efficacy, monkeys are inoculated with non-attenuated virus in an effective volume of 50% monkey infective doses ($MID_{50}$) subcutaneously in the upper arm area.

(4) Laboratory assays: Serum samples are used to determine: (a) the viremic duration by direct viral plaque assay; (b) the titer of dengue or other flavivirus specific antibodies by radio-immunoprecipitation and/or ELISA; and (c) the titer of neutralization antibodies by plaque reduction neutralization test, all tests well known to those skilled in the art of vaccine development.

EXAMPLE 16

Flavivirus Vaccines Attenuated in Humans and Arthropod Vectors

A replication-defective flavivirus as discussed, manufactured, and tested in the Examples above will be replication-defective in arthropod vectors that transmit flaviviruses to humans, and it will possess an attenuated virulence in humans.

While the invention above has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by any patent hereon be limited only by the appended claims and equivalents thereof.

TABLE 4

| Referenced Sequences | |
|---|---|
| SEQ ID NO:1 | PCR primer |
| SEQ ID NO:2 | PCR primer |
| SEQ ID NO:3 | Dengue type 2 3'-SL |
| SEQ ID NO:4 | West Nile 3'-SL |
| SEQ ID NO:5 | DEN2 nucleotides 18 to 62 |
| SEQ ID NO:6 | WN nucleotides 17 to 66 |
| SEQ ID NO:7 | DEN2 nudeotides 1–17 |
| SEQ ID NO:8 | DEN2 nucleotides 63–93 |
| SEQ ID NO:9 | WN nucleotides 1–16 |
| SEQ ID NO:10 | WN nucleotides 67–96 |
| SEQ ID NO:11 | WN nucleotides 63–79 |
| SEQ ID NO:12 | WN nucleotides 67–80 |
| SEQ ID NO:13 | DEN2 nucleotides 80–93 |
| SEQ ID NO:14 | WN nucleotides 81–96 |
| SEQ ID NO:15 | DEN2 nucleotides 7–17 |

TABLE 4-continued

| Referenced Sequences | |
|---|---|
| SEQ ID NO:16 | DEN2 nucleotides 63–73 |
| SEQ ID NO:17 | WN nucleotides 7–16 |
| SEQ ID NO:18 | WN nucleotides 67–75 |
| SEQ ID NO:19 | DEN2 nucleotides 1–7 |
| SEQ ID NO:20 | DEN2 nucleotides 73–79 |
| SEQ ID NO:21 | WN nucleotides 1–7 |
| SEQ ID NO:22 | WN nucleotides 75–80 |
| SEQ ID NO:23 | DEN2 nucleotides 24–29 |
| SEQ ID NO:24 | DEN2 nucleotides 51–56 |
| SEQ ID NO:25 | DEN2 nucleotides 18–29 |
| SEQ ID NO:26 | DEN2 nucleotides 51–62 |
| SEQ ID NO:27 | 3'-terminal 7 nucleotide sequence |
| SEQ ID NO:28 | 3'-terminal substitution nucleotide sequence |

What is claimed is:

1. A mutant replication-defective Dengue virus having a genome with a 3' stem-loop structure substitution, which is defective for replication in a mosquito, wherein said substitution consists of an adenine for a uracil substitution at nucleotide 4 and a uracil for a cytosine substitution at nucleotide 74 to eliminate a U—U unbonded bulge, when counted from the 3' end of said Dengue virus genome.

2. The mutant replication-defective Dengue virus of claim 1, further comprising a deletion of an adenine at nucleotide 7 and a deletion of a uracil at nucleotide 73, when counted from the 3' end of said Dengue virus genome.

3. The mutant replication-defective Dengue virus of claim 1 or 2 wherein said Dengue virus is type 1.

4. An immunogenic composition comprising the mutant replication-defective Dengue virus of claim 3.

5. A method of inducing an immune response comprising administering the immunogenic composition of claim 4 to a human to induce an immune response.

6. The mutant replication-defective Dengue virus of claim 1 or 2 wherein said Dengue virus is type 2.

7. An immunogenic composition comprising the mutant replication-defective Dengue virus of claim 6.

8. A method of inducing an immune response comprising administering the immunogenic composition of claim 7 to a human to induce an immune response.

9. The mutant replication-defective Dengue virus of claim 1 or 2 wherein said Dengue virus is type 3.

10. An immunogenic composition comprising the mutant replication-defective Dengue virus of claim 9.

11. A method of inducing an immune response comprising administering the immunogenic composition of claim 10 to a human to induce an immune response.

12. The mutant replication-defective Dengue virus of claim 1 or 2 wherein said Dengue virus is type 4.

13. An immunogenic composition comprising the mutant replication-defective Dengue virus of claim 12.

14. A method of inducing an immune response comprising administering the immunogenic composition of claim 13 to a human to induce an immune response.

15. An immunogenic composition comprising the mutant replication-defective Dengue virus of claim 1 or 2.

16. A method of inducing an immune response comprising administering the immunogenic composition of claim 15 to a human to induce an immune response.

17. A Dengue virus type 1, 2, 3, and 4-containing immunogenic composition comprising the mutant replication-defective Dengue virus of claim 1 or 2.

18. A method of inducing an immune response comprising administering the immunogenic composition of claim 17 to a human to induce an immune response.

* * * * *